United States Patent
Lee et al.

(10) Patent No.: US 10,712,919 B2
(45) Date of Patent: Jul. 14, 2020

(54) METHOD FOR PROVIDING PHYSIOLOGICAL STATE INFORMATION AND ELECTRONIC DEVICE FOR SUPPORTING THE SAME

(71) Applicant: Samsung Electronics Co., Ltd., Suwon-si, Gyeonggi-do (KR)

(72) Inventors: Eun Hye Lee, Seoul (KR); Eun Ji Ahn, Seoul (KR); Dok Shin Lim, Gwacheon-si (KR); Tae Kyeung Lim, Seoul (KR); Joon Ho Ok, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 31 days.

(21) Appl. No.: 15/233,233

(22) Filed: Aug. 10, 2016

(65) Prior Publication Data

US 2017/0046052 A1 Feb. 16, 2017

(30) Foreign Application Priority Data

Aug. 11, 2015 (KR) ........................ 10-2015-0112878

(51) Int. Cl.
*G06F 3/0484* (2013.01)
*G06F 1/16* (2006.01)
(Continued)

(52) U.S. Cl.
CPC ...... *G06F 3/04845* (2013.01); *A61B 5/02438* (2013.01); *A61B 5/1118* (2013.01); *A61B 5/1123* (2013.01); *A61B 5/165* (2013.01); *A61B 5/4809* (2013.01); *A61B 5/6802* (2013.01); *A61B 5/6898* (2013.01); *A61B 5/742* (2013.01); *G04G 9/0064* (2013.01); *G04G 21/025* (2013.01); *G06F 1/163* (2013.01); *G06F 1/1684* (2013.01); *G06F 1/1694* (2013.01);
(Continued)

(58) Field of Classification Search
CPC ...... A61B 5/0205; A61B 5/11; G04G 21/025; G04G 9/0064; G06F 19/00; G06F 1/163; G06F 1/1684; G06F 1/1694; G06F 3/015; G06F 3/0346; G06F 3/04817; G06F 3/04845; G06F 3/0488; G06F 3/04883; G06K 9/00342
See application file for complete search history.

(56) References Cited

U.S. PATENT DOCUMENTS 7,383,081 B2 * 6/2008 Butt ................. G04G 21/025
 600/519
7,522,999 B2 4/2009 Wence et al.
(Continued)

FOREIGN PATENT DOCUMENTS

JP 2008-234054 A 10/2008
KR 10-2011-0021408 A 3/2011

*Primary Examiner* — Michael J Jansen, II
(74) *Attorney, Agent, or Firm* — Jefferson IP Law, LLP

(57) ABSTRACT

An apparatus and method for providing physiological state information are provided. The apparatus includes a wearable electronic device. The wearable electronic device includes a sensor module configured to measure motion of the wearable electronic device, a display configured to provide a user interface (UI) including movable particles displayed on the display, and a processor configured to reduce the number of the displayed movable particles based on the measured motion of the wearable device.

16 Claims, 16 Drawing Sheets

(51) Int. Cl.

| | | |
|---|---|---|
| *G06F 3/0346* | (2013.01) | |
| *G06F 3/01* | (2006.01) | |
| *G06F 3/0488* | (2013.01) | |
| *G04G 9/00* | (2006.01) | |
| *G06F 3/0481* | (2013.01) | |
| *G06K 9/00* | (2006.01) | |
| *G04G 21/02* | (2010.01) | |
| *A61B 5/11* | (2006.01) | |
| *A61B 5/024* | (2006.01) | |
| *G16H 50/20* | (2018.01) | |
| *A61B 5/16* | (2006.01) | |
| *G16H 20/60* | (2018.01) | |
| *A61B 5/00* | (2006.01) | |
| *G16H 40/63* | (2018.01) | |
| *G16H 20/30* | (2018.01) | |

(52) U.S. Cl.
CPC ............ *G06F 3/015* (2013.01); *G06F 3/0346* (2013.01); *G06F 3/0488* (2013.01); *G06F 3/04817* (2013.01); *G06F 3/04883* (2013.01); *G06K 9/00342* (2013.01); *G16H 20/30* (2018.01); *G16H 20/60* (2018.01); *G16H 40/63* (2018.01); *G16H 50/20* (2018.01)

(56) References Cited

U.S. PATENT DOCUMENTS

| | | | | |
|---|---|---|---|---|
| 8,144,547 | B2* | 3/2012 | Plancon | G04B 19/082 368/10 |
| 8,751,253 | B2* | 6/2014 | Breslau | G06F 19/3406 705/2 |
| 9,019,129 | B2 | 4/2015 | Skinder et al. | |
| 9,259,615 | B2* | 2/2016 | Weast | G06F 19/3481 |
| 9,411,483 | B2* | 8/2016 | Kake | G06F 3/0481 |
| 9,449,365 | B2* | 9/2016 | Roberts | G06T 3/40 |
| 9,449,409 | B2* | 9/2016 | Roberts | G06T 11/206 |
| 9,607,421 | B2* | 3/2017 | Lee | G06T 13/80 |
| 9,818,319 | B2* | 11/2017 | Kwon | G06F 1/163 |
| 9,965,033 | B2* | 5/2018 | Park | G06F 3/014 |
| 10,103,764 | B2* | 10/2018 | Chen | G04G 21/00 |
| 10,194,060 | B2* | 1/2019 | Mistry | H04N 5/2252 |
| 10,241,574 | B2* | 3/2019 | Choi | G06F 1/163 |
| 10,258,288 | B2* | 4/2019 | Penders | A61B 5/721 |
| 10,292,635 | B2* | 5/2019 | Eom | A61B 5/486 |
| 10,423,214 | B2* | 9/2019 | Mistry | G06F 1/329 |
| 10,429,888 | B2* | 10/2019 | Connor | G06F 1/1694 |
| 10,456,623 | B2* | 10/2019 | Weast | A63B 24/0062 |
| 10,463,273 | B2* | 11/2019 | Miller | A61B 5/4875 |
| 10,551,928 | B2* | 2/2020 | Mistry | G06F 3/017 |
| 2006/0064325 | A1* | 3/2006 | Matsumoto | A61B 5/1118 705/3 |
| 2007/0016091 | A1* | 1/2007 | Butt | G04G 21/025 600/519 |
| 2007/0168126 | A1 | 7/2007 | Wence et al. | |
| 2008/0229223 | A1* | 9/2008 | Kake | G06F 3/0481 715/764 |
| 2009/0106049 | A1* | 4/2009 | Breslau | G06F 19/3406 705/3 |
| 2011/0054269 | A1 | 3/2011 | Lee et al. | |
| 2014/0028477 | A1 | 1/2014 | Michalske | |
| 2014/0139637 | A1* | 5/2014 | Mistry | H04N 5/2252 348/46 |
| 2014/0143678 | A1* | 5/2014 | Mistry | G06F 3/017 715/746 |
| 2014/0143737 | A1* | 5/2014 | Mistry | G06F 3/0488 715/854 |
| 2014/0143785 | A1* | 5/2014 | Mistry | G06F 1/163 718/104 |
| 2014/0160078 | A1* | 6/2014 | Seo | G06F 3/017 345/175 |
| 2014/0180454 | A1* | 6/2014 | Weast | G06F 19/3481 700/91 |
| 2014/0221792 | A1* | 8/2014 | Miller | A61B 5/4875 600/309 |
| 2014/0232570 | A1* | 8/2014 | Skinder | G01C 21/165 340/989 |
| 2014/0236633 | A1* | 8/2014 | Breslau | G06F 19/3406 705/3 |
| 2014/0335490 | A1* | 11/2014 | Baarman | A61B 5/002 434/236 |
| 2015/0181087 | A1* | 6/2015 | Mistry | H04N 5/2252 348/158 |
| 2015/0182113 | A1* | 7/2015 | Utter, II | A61B 5/0022 340/539.12 |
| 2015/0182130 | A1* | 7/2015 | Utter, II | A61B 5/0205 600/483 |
| 2015/0193951 | A1* | 7/2015 | Lee | G06T 13/80 345/593 |
| 2015/0248235 | A1* | 9/2015 | Offenberg | G06F 3/04886 715/773 |
| 2015/0265217 | A1* | 9/2015 | Penders | A61B 5/721 600/301 |
| 2015/0294440 | A1* | 10/2015 | Roberts | G06T 3/40 345/666 |
| 2015/0294487 | A1* | 10/2015 | Roberts | G06T 11/206 345/440 |
| 2015/0309535 | A1* | 10/2015 | Connor | G06F 1/163 361/679.03 |
| 2015/0324000 | A1* | 11/2015 | Park | G06F 3/014 345/156 |
| 2016/0008632 | A1* | 1/2016 | Wetmore | A61N 7/00 601/2 |
| 2016/0120460 | A1* | 5/2016 | Eom | A61B 5/486 600/301 |
| 2016/0202759 | A1* | 7/2016 | Choi | G06F 1/163 345/156 |
| 2016/0328023 | A1* | 11/2016 | Mistry | G06F 3/014 |
| 2016/0349790 | A1* | 12/2016 | Connor | G06F 1/1694 |
| 2016/0372016 | A1* | 12/2016 | Kwon | G06F 1/163 |
| 2017/0004639 | A1* | 1/2017 | Roberts | G06T 11/206 |
| 2017/0043217 | A1* | 2/2017 | Lee | G06F 19/3481 |
| 2017/0046052 | A1* | 2/2017 | Lee | G06F 3/0488 |
| 2017/0068407 | A1* | 3/2017 | Wilson | G06F 3/04842 |
| 2017/0093451 | A1* | 3/2017 | Chen | G04G 21/00 |
| 2017/0161007 | A1* | 6/2017 | Francis | G06F 3/1423 |
| 2017/0168610 | A1* | 6/2017 | Myung | G06F 3/044 |
| 2017/0188847 | A1* | 7/2017 | Ahmed | A61B 5/02405 |
| 2017/0231527 | A1* | 8/2017 | Jaeger | A61B 5/11 702/141 |
| 2017/0235922 | A1* | 8/2017 | Weast | G06F 19/3481 434/247 |
| 2017/0273637 | A1* | 9/2017 | Sugiyama | A61B 5/11 |

* cited by examiner

METHOD FOR PROVIDING PHYSIOLOGICAL STATE INFORMATION AND ELECTRONIC DEVICE FOR SUPPORTING THE SAME

CROSS-REFERENCE TO RELATED APPLICATION(S)

This application claims the benefit under 35 U.S.C. §119(a) of a Korean patent application filed on Aug. 11, 2015 in the Korean Intellectual Property Office and assigned Serial number 10-2015-0112878, the entire disclosure of which is hereby incorporated by reference.

TECHNICAL FIELD

The present disclosure relates to an apparatus and method for providing physiological state information via an electronic device, such as a wearable electronic device.

BACKGROUND

Recently, there has been a growing trend towards users who want to improve their physiological states and live healthier. Therefore, many electronic devices (or wearable electronic devices), which provide physiological states in an explicit manner, have been released in the market. For example, electronic devices, which provide a workout time, an amount of workout, or a sleep time, and the like as numeric values or explicitly provide calories in the food and drink taken in by users, have come to the market.

However, the above-mentioned physiological state information may include privacy information. Therefore, to explicitly provide such physiological state information may compromise the privacy of the users.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method for providing physiological state information to provide a user interface (UI) including a display object corresponding to physiological state information and to change the UI or a display object included in the UI based on a change of the physiological state and an electronic device for supporting the same.

In accordance with an aspect of the present disclosure, a wearable electronic device is provided. The wearable electronic device includes a sensor module configured to measure motion of the wearable electronic device, a display configured to provide a UI including a plurality of movable particles, and a processor configured to reduce the number of the plurality of movable particles based on the measured motion of the wearable device.

In accordance with another aspect of the present disclosure, a wearable electronic device is provided. The wearable electronic device includes a sensor module configured to obtain physiological state information, a display configured to provide a UI including a plurality of display objects corresponding to the physiological state information, and a processor configured to change a display state of at least one of the plurality of display objects in response to a change in the physiological state information.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
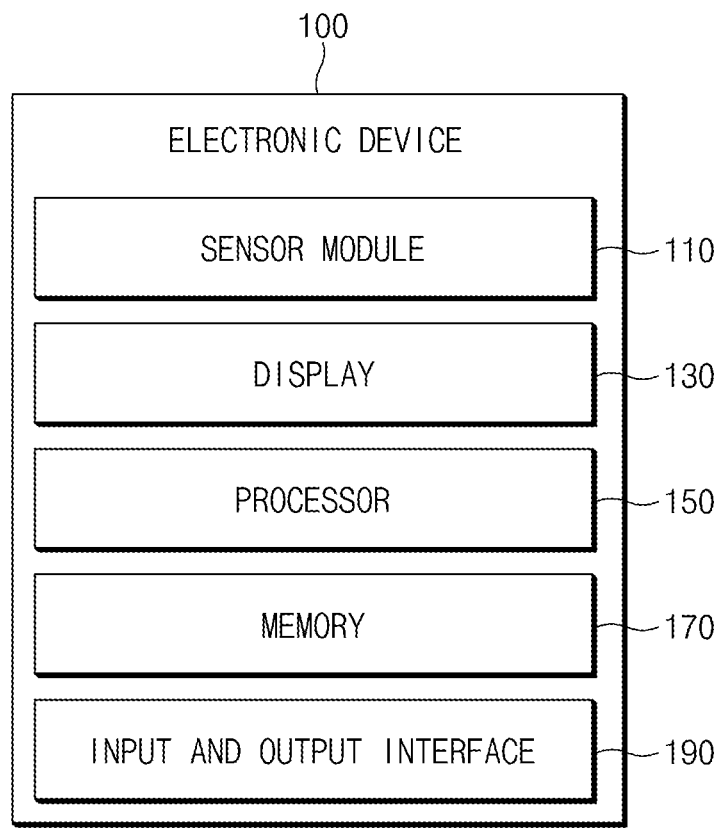
FIG. 1 is a block diagram illustrating a configuration of an electronic device associated with providing physiological state information according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the disclosure disclosed herein, the expressions "have", "may have", "include" and "comprise", or "may include" and "may comprise" used herein indicate existence of corresponding features (e.g., elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The expressions such as "1st", "2nd", "first", or "second", and the like used in various embodiments of the present disclosure may refer to various elements irrespective of the order and/or priority of the corresponding elements, but do not limit the corresponding elements. The expressions may be used to distinguish one element from another element. For instance, both "a first user device" and "a second user device" indicate different user devices from each other irrespective of the order and/or priority of the corresponding elements. For example, a first component may be referred to as a second component and vice versa without departing from the scope of the present disclosure.

It will be understood that when an element (e.g., a first element) is referred to as being "(operatively or communicatively) coupled with/to" or "connected to" another element (e.g., a second element), it can be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there is no intervening element (e.g., a third element).

Depending on the situation, the expression "configured to" used herein may be used as, for example, the expression "suitable for", "having the capacity to", "designed to", "adapted to", "made to", or "capable of". The term "configured to" must not mean only "specifically designed to" hardwarily. Instead, the expression "a device configured to" may mean that the device is "capable of" operating together with another device or other components. For example, a "processor configured to perform A, B, and C" may mean a generic-purpose processor (e.g., a central processing unit (CPU) or an application processor (AP)) which may perform corresponding operations by executing one or more software programs which stores a dedicated processor (e.g., an embedded processor) for performing a corresponding operation.

Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude various embodiments of the present disclosure.

Electronic devices according to various embodiments of the present disclosure may include at least one of, for example, smart phones, tablet personal computers (PCs), mobile phones, video telephones, electronic book readers, desktop PCs, laptop PCs, netbook computers, workstations, servers, personal digital assistants (PDAs), portable multimedia players (PMPs), Moving Picture Experts Group phase 1 or phase 2 (MPEG-1 or MPEG-2) audio layer 3 (MP3) players, mobile medical devices, cameras, or wearable devices. According to various embodiments, the wearable devices may include at least one of accessory-type wearable devices (e.g., watches, rings, bracelets, anklets, necklaces, glasses, contact lenses, or head-mounted-devices (HMDs)), fabric or clothing integral wearable devices (e.g., electronic clothes), body-mounted wearable devices (e.g., skin pads or tattoos), or implantable wearable devices (e.g., implantable circuits).

In various embodiments, the electronic devices may be smart home appliances. The smart home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ and PlayStation™), electronic dictionaries, electronic keys, camcorders, or electronic picture frames.

In various embodiments, the electronic devices may include at least one of various medical devices (e.g., various portable medical measurement devices (e.g., blood glucose meters, heart rate meters, blood pressure meters, or thermometers, and the like), a magnetic resonance angiography (MRA), a magnetic resonance imaging (MRI), a computed tomography (CT), scanners, or ultrasonic devices, and the like), navigation devices, global navigation satellite system (GNSS), event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to various embodiments of the present disclosure, the electronic devices may include at least one of parts of furniture or buildings/structures, electronic boards, electronic signature receiving devices, projectors, or various measuring instruments (e.g., water meters, electricity meters, gas meters, or wave meters, and the like). The electronic devices according to various embodiments of the present disclosure may be one or more combinations of the above-mentioned devices. The electronic devices according to various embodiments of the present disclosure may be flexible electronic devices. Also, electronic devices according to various embodiments of the present disclosure are not limited to the above-mentioned devices, and may include new electronic devices according to technology development Hereinafter, electronic devices according to various embodiments will be described with reference to the accompanying drawings. The term "user" used herein may refer to a person who uses an electronic device or may refer to a device (e.g., an artificial electronic device) that uses an electronic device.

FIG. 1 is a block diagram illustrating a configuration of an electronic device associated with providing physiological state information according to various embodiments of the present disclosure. According to various embodiments, an electronic device 100 may provide physiological state information of its user. For example, the electronic device 100 may provide motion information, sleep information, fluid intake information, heartbeat information, or stress information, and the like. According to an embodiment, the electronic device 100 may provide a user interface (UI) including a display object corresponding to the physiological state information. For example, the electronic device 100 may include various forms of display objects in the UI and may change the UI or the display objects based on the physiological state information. Therefore, the user may verify the changed state of the UI or the display objects to verify a change of a physiological state.

Referring to FIG. 1, the electronic device 100 for performing the above-mentioned function may include a sensor module 110, a display 130, a processor 150, a memory 170, and an input and output interface 190. However, the components of the electronic device 100 shown in FIG. 1 are not limited thereto. According to various embodiments, the electronic device 100 may include additional component(s) other than the above-mentioned components. In various embodiments, at least one of the above-mentioned components of the electronic device 100 may be omitted from the electronic device 100.

The sensor module 110 may measure, for example, a physical quantity or may detect an operation state of the electronic device 100, and may convert the measured or detected information to an electric signal. The sensor module 110 may include, for example, an acceleration sensor, a gyro sensor, a touch sensor, a motion sensor, a heartbeat sensor, or an electrocardiogram (ECG) sensor, and the like. According to an embodiment, the sensor module 110 may collect a movement amount and the like of the electronic device 100 based on the acceleration sensor or the gyro sensor and the like. According to various embodiments, the sensor module 110 may receive a user input (e.g., a touch input) based on the touch sensor and the like. Also, according to another embodiment, the sensor module 110 may collect heart rate information or ECG information and the like based on the heartbeat sensor or the ECG sensor and the like. According to various embodiments, the sensor module 110 may collect motion or shake information of the electronic device 100 based on the motion sensor and the like. According to various embodiments, the sensor module 110 may send the collected information to the processor 150.

The display 130 may output a variety of content (e.g., text, an image, an icon, a video, or a symbol and the like). According to an embodiment, the display 130 may output a UI including a display object corresponding to the physiological state information. According to various embodiments, the display 130 may include a touch screen and may receive, for example, a touch, a gesture, proximity, or a hovering input using an electronic pen or part of a body of the user.

The processor 150 may perform calculation or data processing about control and/or communication of at least another of the components of the electronic device 100. According to various embodiments, the processor 150 may generate physiological state information using sensor information received from the sensor module 110. The physiological state information may include motion information, sleep information, fluid intake information, heartbeat information, or stress information, and the like. According to an embodiment, the processor 150 may generate motion information using a movement amount and the like measured based on the acceleration sensor or the gyro sensor and the like. According to another embodiment, the processor 150 may generate heartbeat information or stress information and the like using heart rate information or ECG information and the like measured based on the heartbeat sensor or the ECG sensor and the like. According to various embodiments, the processor 150 may analyze a user input collected through the input and output interface 190 to generate fluid intake information and the like. For example, if the user inputs an amount of fluid he or she takes in, based on an input means provided from the input and output interface 190, the processor 150 may generate fluid intake information using the amount of fluid taken in by the user.

According to various embodiments, of the present disclosure the processor 150 may generate a UI to be output on the display 130. According to an embodiment, the processor 150 may generate a display object and may include the generated display object in the UI. In this regard, the display object may include a particle object. In various embodiments, the display object may include an image object formed by points, lines, or faces. According to various embodiments, the display object may correspond to the generated physiological state information. According to an embodiment, the display object may be generated in type, color, shape, or size in a different way based on properties of the physiological state information. According to various embodiments, the processor 150 may include another object other than the display object in the UI. According to an embodiment, the processor 150 may further include a time display object and the like in the UI. For example, the processor 150 may include a time display object, indicating a current time, in the UI.

According to various embodiments of the present disclosure, the processor 150 may change the UI. According to an embodiment, the processor 150 may change a background color and the like of the UI. According to various embodiments, the processor 150 may change display objects included in the UI. According to an embodiment, the processor 150 may change the number of the display objects or a location, a shape, a color, or a size and the like of each of the display objects. According to various embodiments, the processor 150 may convert the UI into another UI, rather than changing the UI. For example, the processor 150 may convert a first UI including a first display object into a second UI including a second display object. According to various embodiments, the processor 150 may output the UI on the display 130.

The memory 170 may store, for example, a command or data associated with at least another of the components of the electronic device 100. According to various embodiments, the memory 170 may store the physiological state information. According to an embodiment, the memory 170 may classify and store the physiological state information based on properties of the physiological state information. Also, the memory 170 may store the physiological state information together with time information. For example, the memory 170 may store history information of the physiological state information from a time when the physiological state information is generated.

The input and output interface 190 may play a role as, for example, an interface which may send a command or data, input from the user or another external device, to another component (or other components) of the electronic device 100. Also, input and output interface 190 may output a command or data, received from another component (or other components) of the electronic device 100, to the user or the other external device. The input and output interface 190 may include, for example, a touch panel, a pen sensor (digital pen), a key, or an ultrasonic input unit and the like, as input means. The touch panel may use, for example, at least one of a capacitive type, a resistive type, an infrared type, or an ultrasonic type. The pen sensor may be, for example, part of the touch panel 1352 or may include a separate sheet for recognition. The key may include, for example, a physical button, an optical key, or a keypad and the like. The ultrasonic input unit may allow the electronic device 100 to detect an ultrasonic wave generated by an input tool, through a microphone and to verify data corresponding to the detected ultrasonic wave. The input and output interface 190 may include, for example, a speaker or an earphone and the like, as output means.

According to various embodiments of the present disclosure, a wearable electronic device may include a sensor module configured to measure motion of the wearable electronic device, a display configured to provide a UI including a plurality of movable particles, and a processor configured to reduce the number of the plurality of movable particles based on the measured result.

According to various embodiments of the present disclosure, the processor may be configured to include a notification object, including information about the motion, in the UI if motion of a first level or less continues for a certain time or more.

According to various embodiments of the present disclosure, the processor may be configured to change a background color of the UI if motion which is greater than a second level continues for a certain time or more.

According to various embodiments of the present disclosure, a wearable electronic device may include a sensor module configured to obtain physiological state information, a display configured to provide a UI including a plurality of display objects corresponding to the physiological state information, and a processor configured to change a display state of at least one of the plurality of display objects in response to a change of the physiological state information.

According to various embodiments of the present disclosure, the processor may be configured to specify at least one of the number of the plurality of display objects or a location, a shape, a color, or a size of each of the plurality of display objects in a different way based on properties of the physiological state information.

According to various embodiments of the present disclosure, the sensor module may include an acceleration sensor configured to obtain motion information of the wearable electronic device. The processor may be configured to determine a walking state, a running state, a cycling state, a sitting state, or a sleeping state based on the motion information and to change at least one of the number of the plurality of display objects or a location, a shape, a color, or a size of each of the plurality of display objects in a different way based on the determined state.

According to various embodiments of the present disclosure, the sensor module may include a heartbeat sensor configured to obtain heartbeat information of a user of the wearable electronic device. The processor may be configured to repeatedly change at least one of a shape, a color, or a size of at least one of the plurality of display objects in response to a heartbeat pattern of the user based on the heartbeat information.

According to various embodiments of the present disclosure, the sensor module may include a touch sensor configured to receive a user input associated with setting a fluid intake time. The processor may be configured to change at least one of the number of the plurality of display objects or a location, a shape, a color, or a size of each of the plurality of display objects to be different from the other display objects included in the UI if the fluid intake time arrives or occurs.

According to various embodiments of the present disclosure, the wearable electronic device may further include a touch sensor configured to receive a touch input on the UI. The processor may be configured to provide history information of the display object corresponding to a location of the touch input if the touch input is received.

According to various embodiments of the present disclosure, the wearable electronic device may further include a motion sensor configured to receive a motion input of the wearable electronic device. The processor may be configured to provide recommended activities information if motion of the wearable electronic device meets a specific condition.

Figure 2:
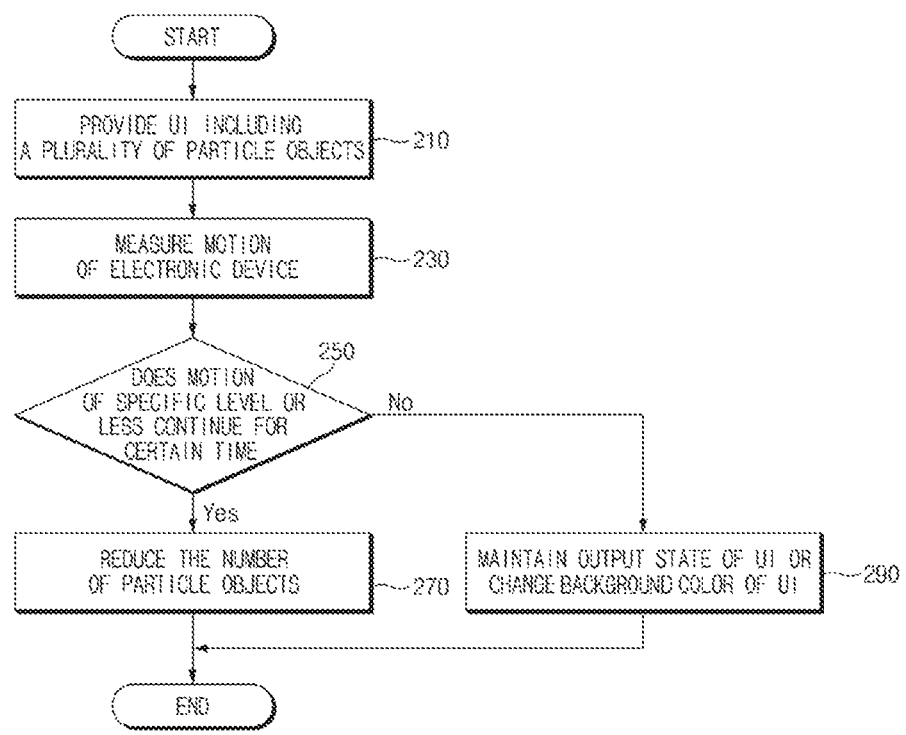
FIG. 2 is a flowchart illustrating an operation method of an electronic device associated with changing a UI based on motion information according to various embodiments of the present disclosure.

FIG. 2 is a flowchart illustrating an operation method of an electronic device associated with changing a UI based on motion information according to various embodiments of the present disclosure. According to various embodiments of the present disclosure, an electronic device 100 of FIG. 1 may change a UI, output on a display 130 of FIG. 1, based on motion information and/or physiological state information.

Referring to FIG. 2, in operation 210, the electronic device 100 may provide a UI including a plurality of particle objects. According to an embodiment, the electronic device 100 may include the plurality of particle objects in different locations of the UI. Also, the electronic device 100 may include the UI in a specific screen (e.g., a home screen) and may output the specific screen on the display 130.

In operation 230, the electronic device 100 may measure its motion based on a sensor module 110 of FIG. 1. According to an embodiment, the electronic device 100 may measure the amount of its movement based on an acceleration sensor and the like and may determine its motion by using the measured amount of movement, acceleration, direction of motion, and the like. According to various embodiments, the electronic device 100 may change locations of the plurality of particle objects based on the motion. According to an embodiment, the electronic device 100 may analyze a direction, an amount, and the like of the motion and may change the locations of the plurality of objects based on the analyzed result. Therefore, the electronic device 100 may obtain the effect of naturally moving the plurality of particle objects on the screen.

In operation 250, the electronic device 100 may determine whether the measured motion continues for a certain period of time at a specific level or less (e.g., a first level or less). According to an embodiment, the electronic device 100 may calculate a degree of the motion as a change amount such as the movement amount and may determine whether the change amount continues for a certain time or more at a specific value or less (e.g., a threshold value or less). According to various embodiments, although some of the change amount during the certain time is greater than the specific value, if most of the change amount is less than or equal to the specific value, the electronic device 100 may determine that the motion continues at the first level or less.

According to various embodiments of the present disclosure, if the motion continues for the certain time at the first level or less, in operation 270, the electronic device 100 may reduce the number of the plurality of particle objects. According to an embodiment, the electronic device 100 may specify a certain number of particle objects at random among the plurality of particle objects included in the UI and may delete the specified particle objects from the UI. According to various embodiments, the electronic device 100 may gradually reduce the number of the plurality of particle objects. For example, after performing operation 270, the electronic device 100 may return to operation 230. Therefore, the electronic device 100 may continue measuring its motion. If the measured motion continues for a certain time at the first level or less, the electronic device 100 may gradually reduce the number of the plurality of particle objects.

According to various embodiments of the present disclosure, if the motion does not continue for the certain time at the first level or less, in operation 290, the electronic device 100 may maintain an output state of the UI or may change a background color of the UI. According to various embodiments, the electronic device 100 may determine whether motion which is greater than a specific level (or a second level) continues for a certain time. According to an embodiment, if the motion is greater than the second level during the certain time or more, the electronic device 100 may determine that a user of the electronic device 100 is in a workout state. In this case, the electronic device 100 may change a background color of the UI.

According to various embodiments of the present disclosure, if the motion is greater than the first level during a certain time or more in a state where the number of the plurality of particle objects is reduced, the electronic device 100 may gradually restore the reduced number of the plurality of particle objects. Also, if the motion continues for a certain time or more at the second level or less in a state where the background color of the UI is changed, the electronic device 100 may restore the changed background color to a previous color.

Figure 3:
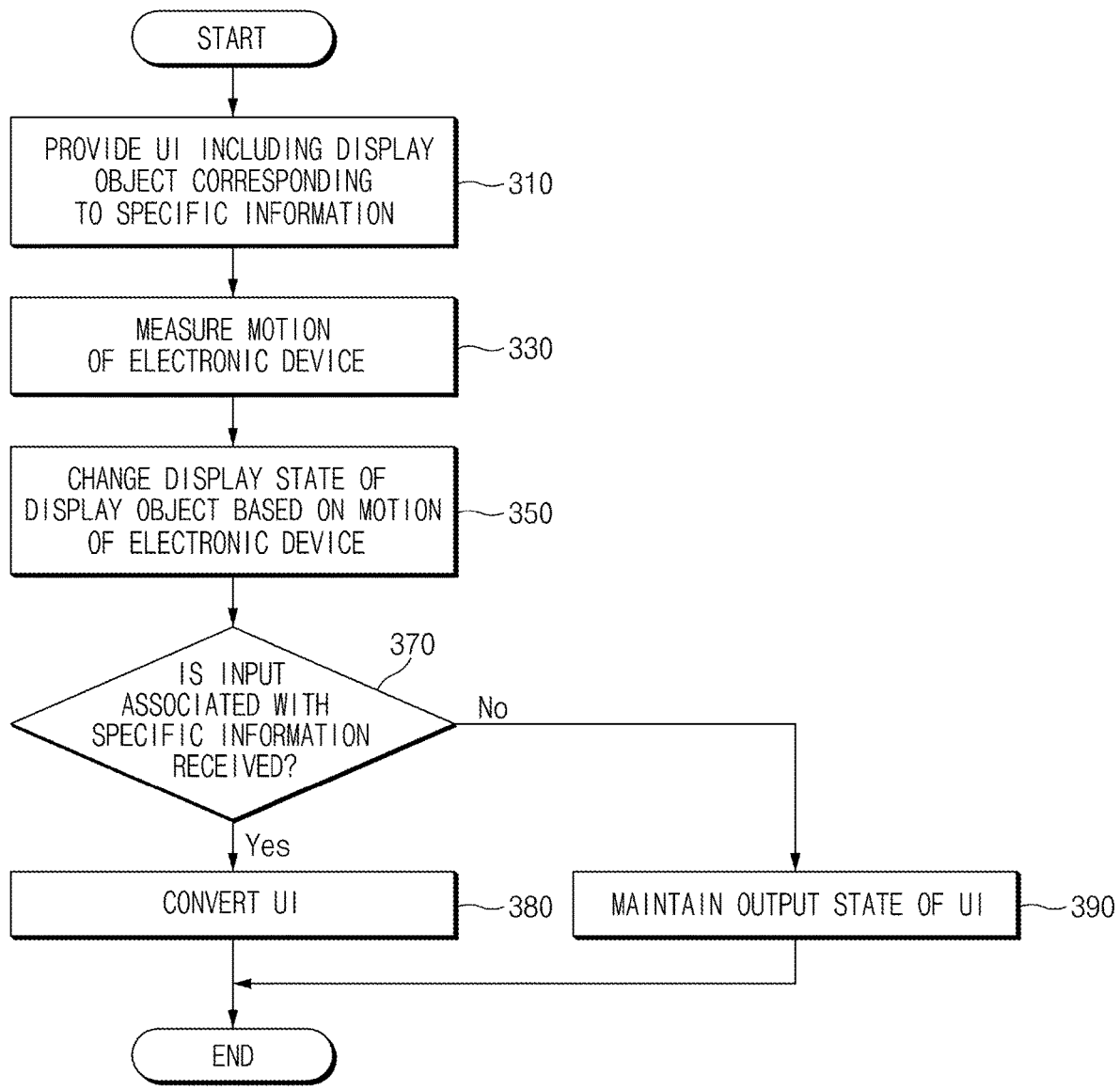
FIG. 3 is a flowchart illustrating an operation method of an electronic device associated with providing physiological state information according to various embodiments of the present disclosure.

FIG. 3 is a flowchart illustrating an operation method of an electronic device associated with providing physiological state information according to various embodiments of the present disclosure. According to various embodiments, an electronic device 100 of FIG. 1 may change a UI, output on a display 130 of FIG. 1, based on another information included in physiological state information, as well as motion information.

Referring to FIG. 3, in operation 310, the electronic device 100 may provide a UI (e.g., a first UI) including a display object corresponding to specific information (e.g., information included in the physiological state information). According to an embodiment of the present disclosure, the electronic device 100 may output the first UI, including display objects which vary in number, location, shape, color, or size and the like based on motion information, sleep information, fluid intake information, heartbeat information, or stress information and the like, on the display 130. For example, the electronic device 100 may generate display objects, corresponding to motion information, sleep information, fluid intake information, heartbeat information, and stress information, with a first color (e.g., green), a second color (e.g., purple), a third color (e.g., blue), a fourth color (e.g., pink), and the fifth color (e.g., gray), respectively, and may include the display objects in the first UI by the first number of display objects, the second number of display objects, the third number of display objects, the fourth number of display objects, and the fifth number of display objects, respectively.

In operation 330, the electronic device 100 may measure its motion. According to an embodiment, the electronic device 100 may measure its movement amount based on an acceleration sensor and the like and may determine the motion based on a change amount of the movement amount.

In operation 350, the electronic device 100 may change display states of the display objects based on the motion of the electronic device 100. According to an embodiment, the electronic device 100 may change locations of the display objects in response to a direction and size of the motion. According to various embodiments, the electronic device 100 may analyze a pattern of the motion. According to an embodiment, the electronic device 100 may analyze a direction, a size, or a change amount and the like of the motion and may determine a type of the motion based on the analyzed result. For example, the electronic device 100 may classify the type of the motion into a walking state, a running state, a cycling state, a sitting state, or a sleeping state and the like. According to various embodiments, the electronic device 100 may change the number of the display objects or a location, a shape, a color, or a size of each of the display objects based on the type of the motion. According to an embodiment, if the type of the motion indicates the sleeping state, the electronic device 100 may increase the number of display objects corresponding to the sleeping information.

In operation 370, the electronic device 100 may determine whether an input associated with the specific information is received. If the input associated with the specific information is received, in operation 380, the electronic device 100 may convert a UI. According to various embodiments, if an input associated with heartbeat information (e.g., a sensor input based on measurement of a heart rate) from a sensor module 110 of FIG. 1 is received, the electronic device 100 may generate a UI (e.g., a second UI) including a display object corresponding to the heartbeat information and may convert the previously output first UI into the newly generated second UI. In this regard, the electronic device 100 may arrange and output display objects, corresponding to other physiological state information, around the display object corresponding to the heartbeat information at a certain spaced distance on the second UI. According to various embodiments, the electronic device 100 may generate the display object corresponding to the heartbeat information to be relatively larger in size than display objects corresponding to other physiological state information and may include the generated display object in the second UI.

According to various embodiments of the present disclosure, the electronic device 100 may receive a user input, associated with fluid intake information, based on an input and output interface 190 of FIG. 1. For example, the electronic device 100 may receive a fluid intake information from its user, and it may generate the second UI, including a display object corresponding to the fluid intake information, based on the fluid intake, and may convert the first UI into the second UI. According to various embodiments, the electronic device 100 may change and output display objects in the previously output first UI, rather than converting the first UI into the second UI. For example, the electronic device 100 may change the number of display objects corresponding to the specific information, or a location, a shape, a color, or a size and the like of each of the display objects among display objects included in the first UI and may output the changed display objects.

According to various embodiments of the present disclosure, if the input associated with the specific information is not received, in operation 390, the electronic device 100 may maintain an output state of the previously output first UI. According to various embodiments, if a certain time elapses after operation 380 is performed, the electronic device 100 may restore the converted UI to the previous UI. For example, the electronic device 100 may restore the second UI to the first UI.

Figure 4:
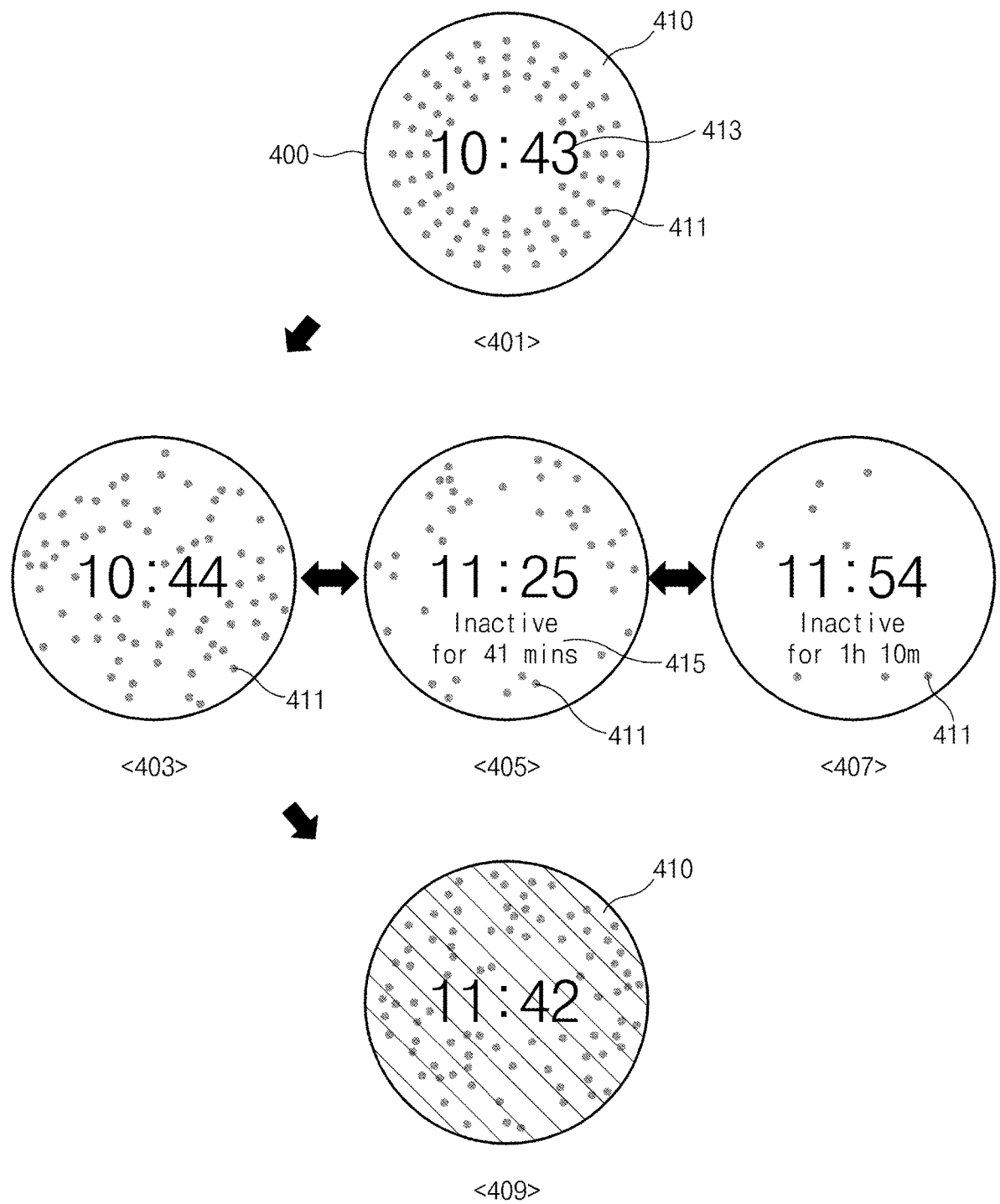
FIG. 4 is a drawing illustrating an operation of changing a user interface (UI) according to various embodiments of the present disclosure.

FIG. 4 is a drawing illustrating an operation of changing a user interface (UI) according to various embodiments of the present disclosure.

Referring to FIG. 4, an electronic device 100 (e.g., a wearable electronic device) of FIG. 1 may output a UI 410, including a plurality of particle objects 411, on its display 400. According to an embodiment, the electronic device 100 may arrange the plurality of particle objects 411 to be displayed on different locations of the UI 410 on the display 400. Also, in a first state 401, the electronic device 100 may arrange the plurality of particle objects 411 in a certain form. For example, the electronic device 100 may fix locations of the plurality of particle objects 411 and may output the fixed particle objects on a screen before user authentication is performed. Alternatively, the electronic device 100 may not output the plurality of particle objects 411 before the user authentication is performed.

According to various embodiments of the present disclosure, when the user authentication is performed and when a specific screen (e.g., a home screen) is output, in a second state 403, the electronic device 100 may change locations of the plurality of particle objects 411 at random and may output the plurality of changed particle objects 411. Also, the electronic device 100 may continue changing locations of the plurality of particle objects 411. According to an embodiment, the electronic device 100 may change locations of the plurality of objects 411 using its motion information measured based on its acceleration sensor and the like. For example, the electronic device 100 may change locations of the plurality of particle objects 411 to correspond to a movement direction and size included in the motion information.

According to various embodiments of the present disclosure, the electronic device 100 may change the number of the plurality of objects 411, included in the UI 410, based on the motion information. According to an embodiment, if motion of the electronic device 100 continues for a certain time at a specific level or less (e.g., a first level or less), in a third state 405, the electronic device 100 may reduce the number of the plurality of particle objects 411. According to various embodiments, the electronic device 100 may further include a notification object 415, including the motion information or information about a time when motion of the electronic device 100 continues at the first level or less, in the UI 410. According to various embodiments, the electronic device 100 may output the notification object 415 using text or an image and the like. In various embodiments, the electronic device 100 may output a voice corresponding to the notification object 415. In addition, according to various embodiments, the electronic device 100 may further include a time display object 413, as a background in the display 400, as illustrated in FIG. 4.

According to various embodiments of the present disclosure, the electronic device 100 may gradually decrease the number of the plurality of objects 411 based on the motion information. According to an embodiment, the electronic device 100 may constantly measure a time when motion of the electronic device 100 continues at the first level or less and may gradually decrease the plurality of particle objects 411 by the specific number of particle objects at intervals of a certain time. As shown in FIG. 4, if the motion of the first level or less continues for the certain time in the second state 403, in the third state 405, the electronic device 100 may decrease the plurality of particle objects 411 by the specific number of particle objects. If the motion of the first level or less continues for the certain time in the third state 405, as described in a fourth state 407, the electronic device 100 may decrease the plurality of particle objects 411 again by the specific number of particle objects. According to various embodiments, the electronic device 100 may continue with the above-mentioned function of decreasing the plurality of particle objects 411, until the plurality of particle objects 411 are of the certain number of particle objects (e.g., 0).

According to various embodiments of the present disclosure, the electronic device 100 may gradually increase the number of the plurality of particle objects 411 based on the motion information. According to an embodiment, if the motion of the electronic device 100 which is greater than the first level continues for a certain time, the electronic device 100 may gradually increase the number of the plurality of particle objects 411 included in the UI 410. For example, the electronic device 100 may be changed from the fourth state 407 to the third state 405 based on the motion information and may be changed from the third state 405 to the second state 403. According to various embodiments, the electronic device 100 may be immediately changed from the second state 403 to the fourth state 407 or from the fourth state 407 to the second state 403, rather than performing the process of being sequentially changed from the second state 403 to the fourth state 407 or from the fourth state 407 to the second state 403 based on the motion information.

According to various embodiments of the present disclosure, the electronic device 100 may change a background color of the UI 410 based on the motion information. According to an embodiment, if motion of the electronic device 100, which is greater than a specific level (or a second level), continues for a certain time, in a fifth state 409, the electronic device 100 may change a background color of the UI 410. If the motion of the electronic device 100 is greater than the second level during a certain time or more, the electronic device 100 may determine that its user is in a workout state. In this case, the workout may change a background color of the UI 410. According to various embodiments, after performing the above-mentioned function of changing the background color of the UI 410, if the motion of the electronic device 100 continues for a certain time at the second level or less, the electronic device 100 may restore the changed background color of the UI 410 to a background color in the second state 403.

Figure 5A:
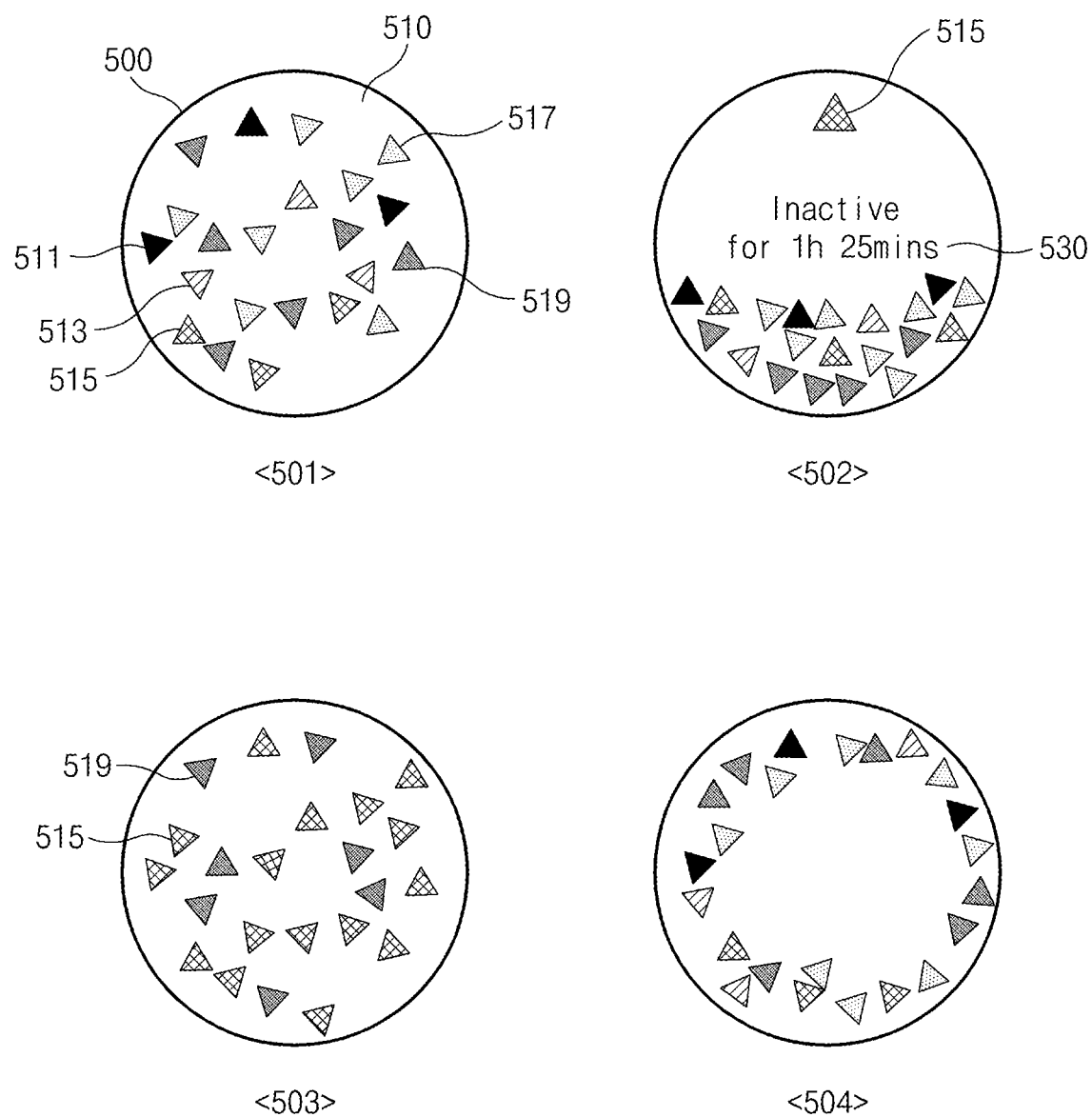
FIG. 5A is a drawing illustrating an operation of providing physiological state information associated with motion information according to various embodiments of the present disclosure.

FIG. 5A is a drawing illustrating an operation of providing physiological state information associated with motion information according to various embodiments of the present disclosure.

Referring to FIG. 5A, an electronic device 100 of FIG. 1 may include a display object, corresponding to physiological state information, in a UI 510 and may output the UI 510 on its display 500. According to an embodiment, the electronic device 100 may include display objects in the UI 510 to vary in number, location, shape, color, or size and the like based on properties of the physiological state information. For example, in a first state 501, the electronic device 100 may include first display objects 511 corresponding to heartbeat information, second display objects 513 corresponding to sleep information, third display objects 515 corresponding to motion information, fourth display objects 517 corresponding to stress information, and fifth display objects 519 corresponding to fluid intake information in the UI 510 to vary in number, location, shape, color, or size and the like.

According to various embodiments of the present disclosure, the electronic device 100 may change locations of the display objects based on motion information. According to an embodiment, the electronic device 100 may change locations of the display objects at random based on motion of the electronic device 100, measured based on its acceleration sensor and the like. Also, if motion of the electronic device 100 continues for a certain time at a specific level or less (e.g., a first level or less), in a second state 502, the electronic device 100 may move the display objects to a lower end of a screen. For example, if the motion of the first level or less continues for a certain time, the electronic device 100 may determine that its user in a sitting state and may move the display objects to the lower end of the screen. Therefore, the user may verify an effect in which the display objects fall to the lower end of the screen.

According to various embodiments of the present disclosure, the electronic device 100 may locate at least one of the third display objects 515, corresponding to motion information, on an upper center region of the screen in a state where the display objects are arranged on the lower end of the screen. In various embodiments, the electronic device 100 may continue to change an output state of at least one of the third display objects 515 located on the upper center region of the screen. For example, the electronic device 100 may continue to change a location, a shape, a color, or a size and the like of each of the third display objects 515 such that the third display objects 515 have a blinking effect. According to various embodiments, the electronic device 100 may further include a notification object 530, including the motion information or information about a time when motion of the electronic device 100 continues at the first level or less, in the UI 510.

According to various embodiments of the present disclosure, if motion of the electronic device 100, which is greater than a specific level (e.g., a second level), continues for a certain time, in a third state 503, the electronic device 100 may delete the other display objects from the UI 510 except for display objects associated with the motion information. For example, if the motion which is greater than the second level continues for the certain time, the electronic device 100 may determine that the user is in a workout state and may delete the other display objects from the UI 510 except for the third display object 515 corresponding to the motion information or the fifth display object 519 corresponding to the fluid intake information. According to various embodiments, the electronic device 100 may increase the number of display objects associated with motion information. In various embodiments, the electronic device 100 may generate a new UI including only the display objects associated with the motion information and may convert the previously output UI 510 into the newly generated UI.

According to various embodiments of the present disclosure, in a fourth state 504, the electronic device 100 may arrange display objects on a rim of a screen at a time when the motion of the electronic device 100, which is greater than the second level, continues for a specific time or more or when the motion is reduced to the second level or less in a state where the motion is greater than the second level.

Referring to FIG. 5A, in an embodiment of the present disclosure the display objects are arranged on the rim of the screen, as in the fourth state 504. However, various embodiments of the present disclosure are not limited thereto. According to various embodiments, the electronic device 100 may repeatedly perform a function of moving the display objects from the rim of the screen to the center of the screen or from the center to the rim. Therefore, the user may verify the effect of repeatedly reducing and expanding the display objects to be similar to heart beat.

Figure 5B:
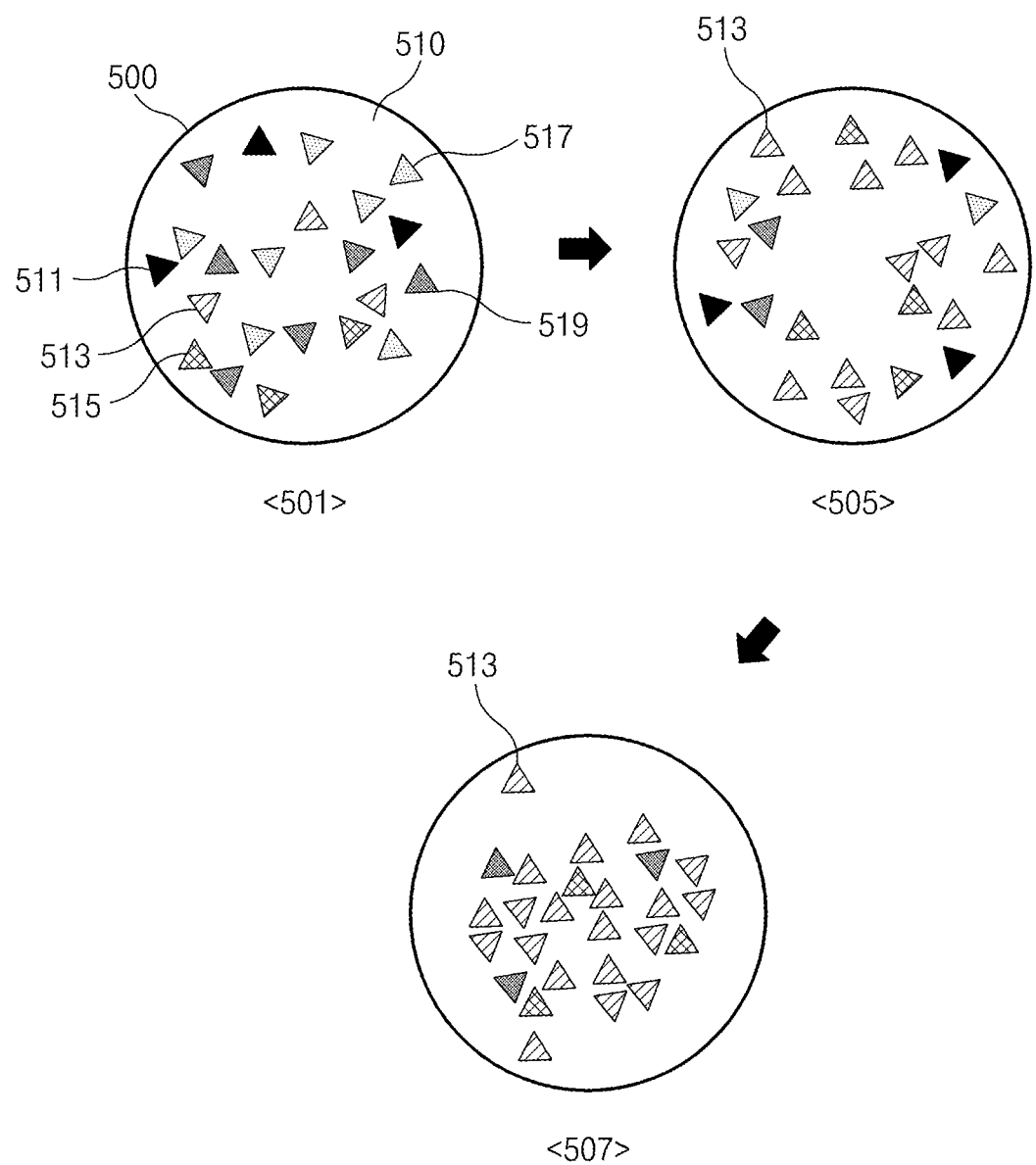
FIG. 5B is a drawing illustrating an operation of providing physiological state information associated with sleep information according to various embodiments of the present disclosure.

FIG. 5B is a drawing illustrating an operation of providing physiological state information associated with sleep information according to various embodiments of the present disclosure.

Referring to FIG. 5B, if motion of an electronic device 100 of FIG. 1 continues for a certain time at a specific level or less (e.g., a third level or less) in a first state 501, as described in a fifth state 505, the electronic device 100 may gradually delete the other display objects except for display objects associated with sleep information. For example, if the motion of the third level or less continues for the certain time, the electronic device 100 may determine that its user is in a sleeping state and may gradually delete the other display objects from a UI 510 except for second display objects 513 and the like corresponding to sleep information. According to various embodiments, the electronic device 100 may determine the sleeping state by additionally using time information. For example, the electronic device 100 may determine the sleeping state using information about a time when the user takes sleep. According to various embodiments, the electronic device 100 may increase the number of the second display objects 513. In various embodiments, the electronic device 100 may generate a new UI including only display objects associated with sleep information and may convert a previously output UI 510 into the newly generated UI.

According to various embodiments, in a sixth state 507, the electronic device 100 may gradually move display objects associated with sleep information to the center of a screen. According to various embodiments, if motion which is greater than the third level continues for a certain time in the sixth state 507 or if a specific user input (or a specific touch input) is received in the sixth state 507, the electronic device 100 may change a location, a shape, a color, or a size and the like of each of at least some of display objects, located on the center of the screen.

Figure 6A:
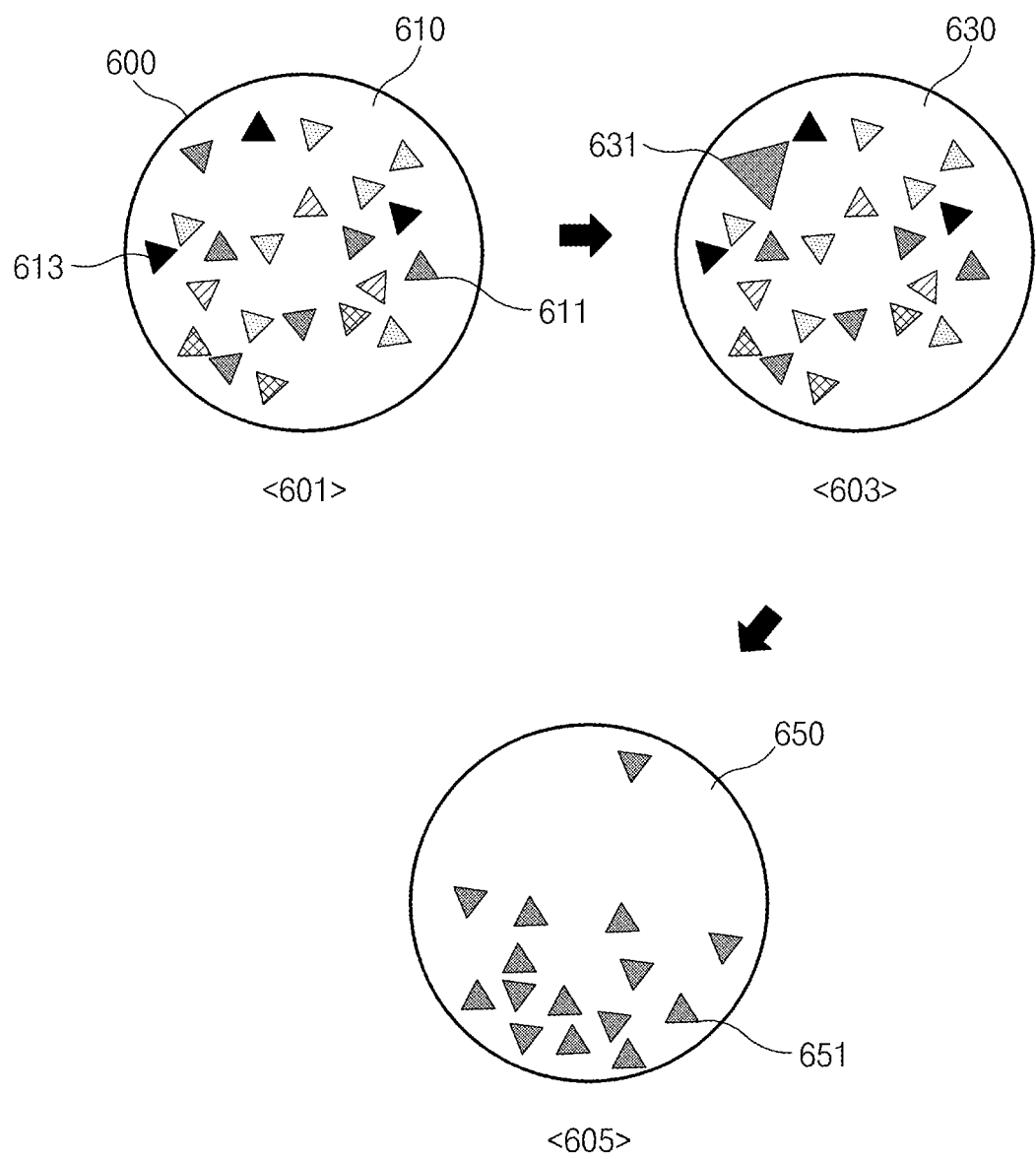
FIG. 6A is a drawing illustrating an operation of providing physiological state information associated with fluid intake information according to various embodiments of the present disclosure.

FIG. 6A is a drawing illustrating an operation of providing physiological state information associated with fluid intake information according to various embodiments of the present disclosure.

Referring to FIG. 6A, an electronic device 100 of FIG. 1 may include a display object, corresponding to physiological state information, in a UI (e.g., a first UI 610) and may output the UI on its display 600. For example, in a first state 601, the electronic device 100 may include display objects, specified to differ in number, location, shape, color, or size and the like based on properties of the physiological state information, in the first UI 610. The first state 601 in FIG. 6A may be the same or similar to a first state 501 in FIG. 5A. For example, the electronic device 100 may include first display objects 613 corresponding to heartbeat information, second display objects corresponding to sleeping information, third display objects corresponding to motion information, fourth display objects corresponding to stress information, and fifth display objects 611 corresponding to fluid intake information to vary in number, location, shape, color, or size, in the first UI 610.

According to various embodiments, if a specific time elapses in the first state 601, the electronic device 100 may provide a UI (e.g., a second UI 630) including at least one display object corresponding to information indicating one of properties of the physiological state information, the at least one display object being generated to differ from a display object corresponding to information indicating other properties. For example, if a fluid intake time set by a user of the electronic device 100 arrives or occurs, the electronic device 100 may generate a sixth display object 631 corresponding to fluid intake information to differ in number, location, shape, color, or size and the like from the other display objects and may include the generated sixth display object 631 in the second UI 630.

Referring to FIG. 6A, an embodiment is exemplified as the electronic device 100 may generate and output the sixth display object 631 in a second state 603 to be larger in size than the other display objects. According to various embodiments, the electronic device 100 may change the number of the fifth display objects 611 corresponding to the fluid intake information, included in the first UI 610, or a location, a shape, a color, or a size and the like of each of the fifth display objects 611 and may output the changed fifth display object 611, rather than converting the first UI 610 into the second UI 630 and providing the second UI 630.

According to various embodiments of the present disclosure, if verifying a fluid intake state, in a third state 605, the electronic device 100 may provide a UI (e.g., a third UI 650) including only display objects (e.g., seventh display objects 651) associated with fluid intake information. In this regard, the electronic device 100 may verify the fluid intake state based on a sensor module 110 or an input and output interface 190 of FIG. 1. For example, the electronic device 100 may receive information, indicating that the user takes in fluids, from him or her. According to various embodiments, the electronic device 100 may move the seventh display objects 651 at random at a specific speed from a lower end of a screen to an upper end of the screen. Therefore, the user may verify the effect that the seventh display objects 651 bound up. In various embodiments, the electronic device 100 may change a shape, a color, or a size and the like of each of the seventh display objects 651 while changing a location of each of the seventh display objects 651.

Figure 6B:
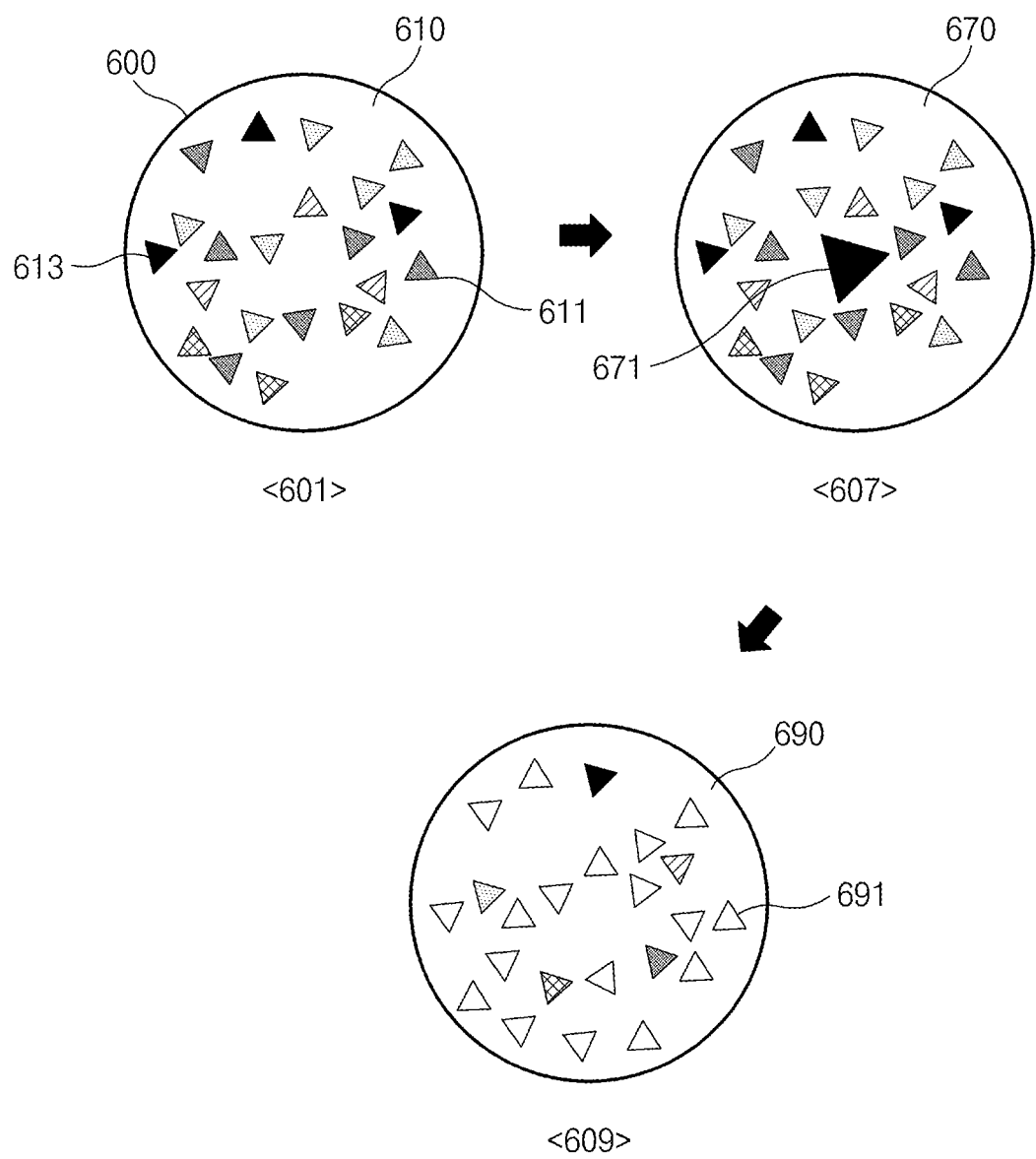
FIG. 6B is a drawing illustrating an operation of providing physiological state information associated with heartbeat information according to various embodiments of the present disclosure.

FIG. 6B is a drawing illustrating an operation of providing physiological state information associated with heartbeat information according to various embodiments of the present disclosure.

Referring to FIG. 6B, if an input associated with specific physiological state information is received in a first state 601, an electronic device 100 of FIG. 1 may provide a UI (e.g., a fourth UI 670) including a display object corresponding to the physiological state information, the display object being generated to differ from a display object corresponding to physiological state information of other properties. For example, if an input for measuring a heart rate is received, the electronic device 100 may generate an eighth display object 671 corresponding to heartbeat information to differ in number, location, shape, color, or size and the like from the other display objects and may include the generated eighth display object 671 in the fourth UI 670.

Referring to FIG. 6B, an embodiment is exemplified as the electronic device 100 may generate and output the eighth display object 671 to be relatively larger in size than the other display objects in a fourth state 607. Also, the electronic device 100 may move and output the eighth display object 671 to the center of a screen. According to various embodiments, the electronic device 100 may repeatedly change a shape, a color, or a size and the like of the eighth display object 671 to correspond to the heartbeat pattern (e.g., a pattern of repeatedly reducing and expanding the eighth display object 671). Therefore, a user of the electronic device 100 may verify the effect that the eighth display object 671 is repeatedly reduced and expanded to be similar to heartbeat.

According to various embodiments of the present disclosure, if the number of inputs for measuring heart rates is greater than a specific number of times, the electronic device 100 may perform the above-mentioned function only if receiving an input corresponding to a heart rate measurement value included within a specific range (e.g., a range of a heart rate which may be indicated by the user). According to various embodiments, the electronic device 100 may change the number of first display objects 613 corresponding to heartbeat information, included in the first UI 610, or a location, a shape, a color, or a size and the like of each of the first display objects 613 and may output the changed first display objects 613.

According to various embodiments, if the measurement of the heart rate is completed, the electronic device 100 may determine a stress level of the user. In various embodiments, the electronic device 100 may determine a stress level using sensor information measured based on its heartbeat sensor or its ECG sensor and the like. According to various embodiments, if determining the stress level of the user, in a fifth state 609, the electronic device 100 may provide a UI (e.g., a fifth UI 690) including only display objects (e.g., ninth display objects 691) associated with stress information. According to an embodiment, the electronic device 100 may output the ninth display objects 691 to vary in number based on the stress level.

According to various embodiments, the electronic device 100 may change the number of fourth display objects corresponding to stress information, included in the first UI 610, or a location, a shape, a color, or a size and the like of each of the fourth display objects and may output the changed fourth display objects, rather than converting the first UI 610 into the fifth UI 690 and providing the changed fifth UI 690. According to various embodiments, the electronic device 100 may change display objects included in the first UI 610 to be the same or similar to the fourth display objects and may output the changed display objects.

Figure 7:
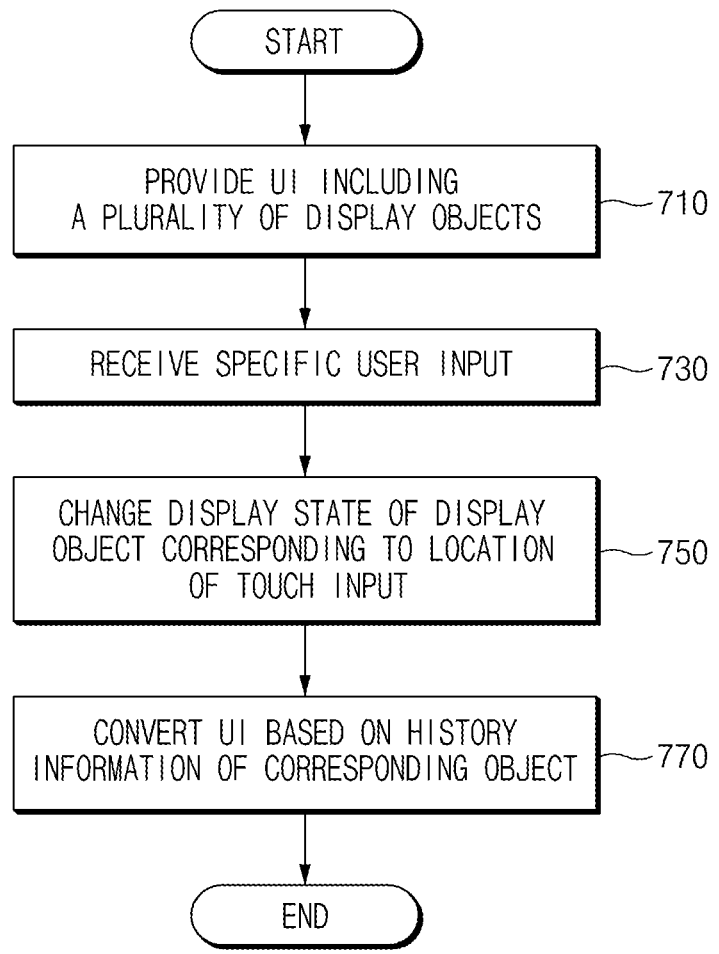
FIG. 7 is a flowchart illustrating an operation method of an electronic device associated with providing history information of a physiological state according to various embodiments of the present disclosure.

FIG. 7 is a flowchart illustrating an operation method of an electronic device associated with providing history information of a physiological state according to various embodiments of the present disclosure.

Referring to FIG. 7, in operation 710, an electronic device 100 of FIG. 1 may provide a UI including a plurality of display objects. According to an embodiment, the electronic device 100 may include the UI, including the plurality of display objects corresponding to physiological state information, in a specific screen (e.g., a home screen) and may output the specific screen on a display 130 of FIG. 1.

In operation 730, the electronic device 100 may receive a specific user input on the UI. According to an embodiment, the electronic device 100 may receive a touch input for touching a certain area of the UI. According to various embodiments, the electronic device 100 may analyze the touch input. For example, a location and time of the touch input or the number of touch objects (e.g., fingers of a user of the electronic device 100). Also, the electronic device 100 may detect a display object corresponding to the location of the touch input. For example, the electronic device 100 may detect a display object output on the location of the touch input or a display object output on a location adjacent to the location of the touch input.

In operation 750, the electronic device 100 may change a display state of a display object corresponding to the location of the touch input. For example, the electronic device 100 may change a location, a shape, a color, or a size and the like of the detected display object.

According to various embodiments, if the touch input is ended (e.g., if a finger of the user is detached from a screen) or if a user input for selecting the detected display object is received, in operation 770, the electronic device 100 may provide history information of the corresponding display object. According to an embodiment, the electronic device 100 may collect history information about the display object from a memory 170 of FIG. 1. Also, the electronic device 100 may generate a UI including information about a change of the display object in number, location, shape, color, or size and the like from a time when the display object is generated to a time when the display object is specified (e.g., a time when the touch input occurs) based on the history information and may convert a previously output UI into the newly generated UI.

Figure 8:
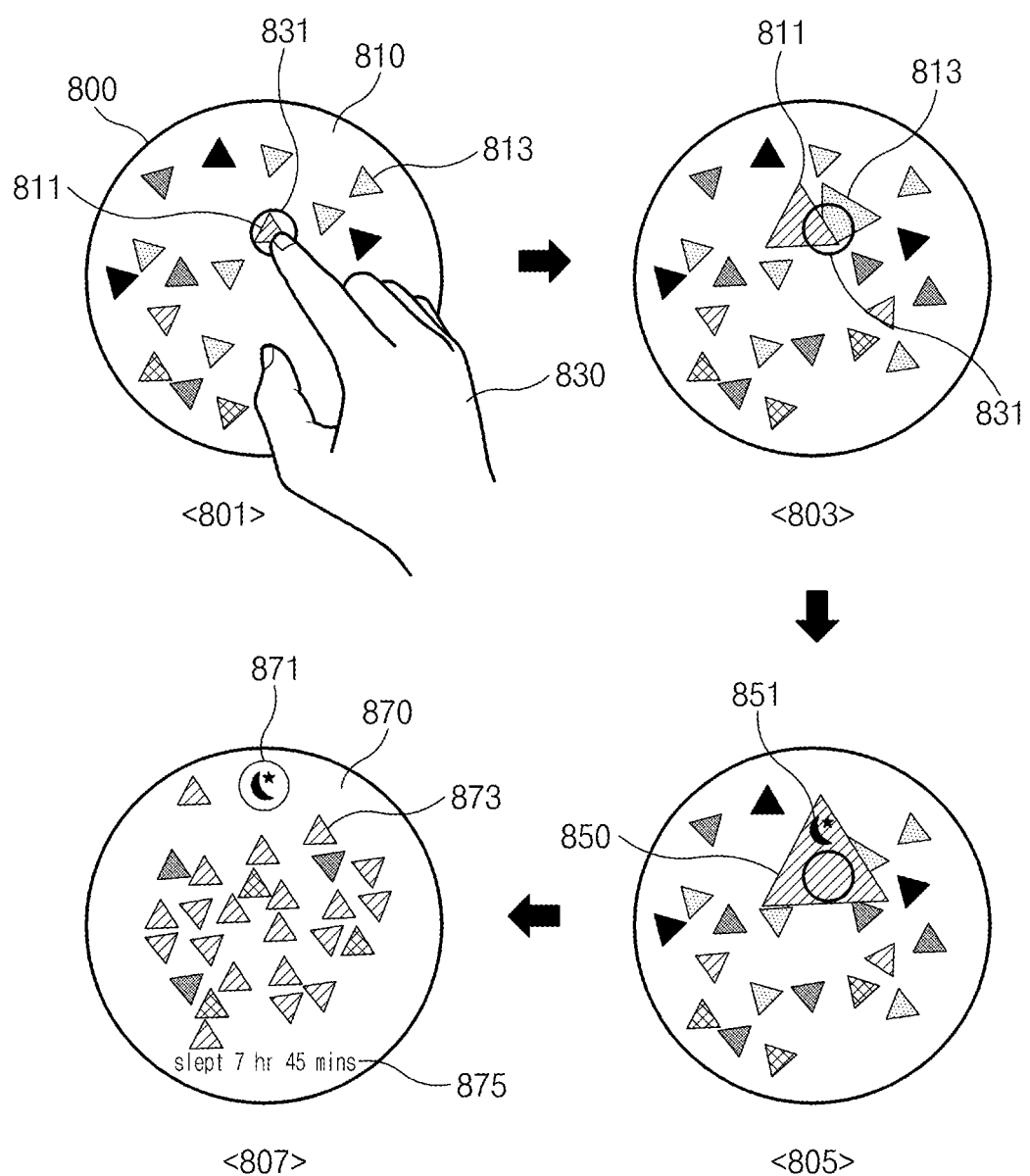
FIG. 8 is a drawing illustrating an operation of providing history information of a physiological state according to various embodiments of the present disclosure.

FIG. 8 is a drawing illustrating an operation of providing history information of a physiological state according to various embodiments of the present disclosure.

Referring to FIG. 8, in a first state 801, an electronic device 100 of FIG. 1 may include a plurality of display objects, corresponding to physiological state information, in a UI 810 and may output the UI 810 on its display 800. According to various embodiments, if a user input (e.g., a touch input 830) on the UI 810 is received, the electronic device 100 may analyze the touch input 830.

The electronic device 100 may change a location, a shape, a color, or a size and the like of each of the plurality of display objects based on the result of analyzing the touch input 830. For example, in a second state 803, the electronic device 100 may change a display state of a display object corresponding to an input location 831 of the touch input 830. Referring to FIG. 8, an embodiment is exemplified as a first display object 811 corresponding to the input location 831 and a second display object 813 are changed to be relatively larger in size than the other display objects. According to various embodiments, the electronic device 100 may change a size of the first display object 811 or the second display object 813 to be gradually larger in size based on duration of the touch input 830 (e.g., a time when a user of the electronic device 100 contacts or hovers over a screen with his or her finger).

According to various embodiments of the present disclosure, if the duration of the touch input 830 is over a certain time or if a certain time elapses after the touch input 830 occurs, in a third state 805, the electronic device 100 may change a display object (e.g., the first display object 811), output on the closest location from the input location 831, to a third display object 850 and may output the changed third display object 850. The third display object 850 may correspond to the same or similar physiological state information to the display object (e.g., the first display object 811) before being changed. In various embodiments, the third display object 850 may include an image or icon object 851 indicating properties of the physiological state information. Referring to FIG. 8, an embodiment is exemplified as the third display object 850 corresponding to sleep information includes an image object (e.g., a moon or star image object) associated with sleep.

According to various embodiments, if the touch input 830 is ended or if a user input for selecting the third display object 850 is received, the electronic device 100 may provide history information of physiological state information corresponding to the third display object 850. According to an embodiment, in a fourth state 807, the electronic device 100 may generate and output a UI 870 including a display object 873 indicating a change degree of physiological state information selected based on the history information. Referring to FIG. 8, an embodiment is exemplified as the electronic device 100 outputs display objects indicating a change of a sleeping state based on history information of selected sleep information. According to various embodiments, providing the history information, the UI 870 may include an image or icon object 871 indicating properties of the selected physiological state information and may further include a notification object 875 associated with the physiological state information. Referring to FIG. 8, an embodiment is exemplified as the UI 870 which provides the history information of the sleep information includes a text object indicating the total sleep time.

Figure 9:
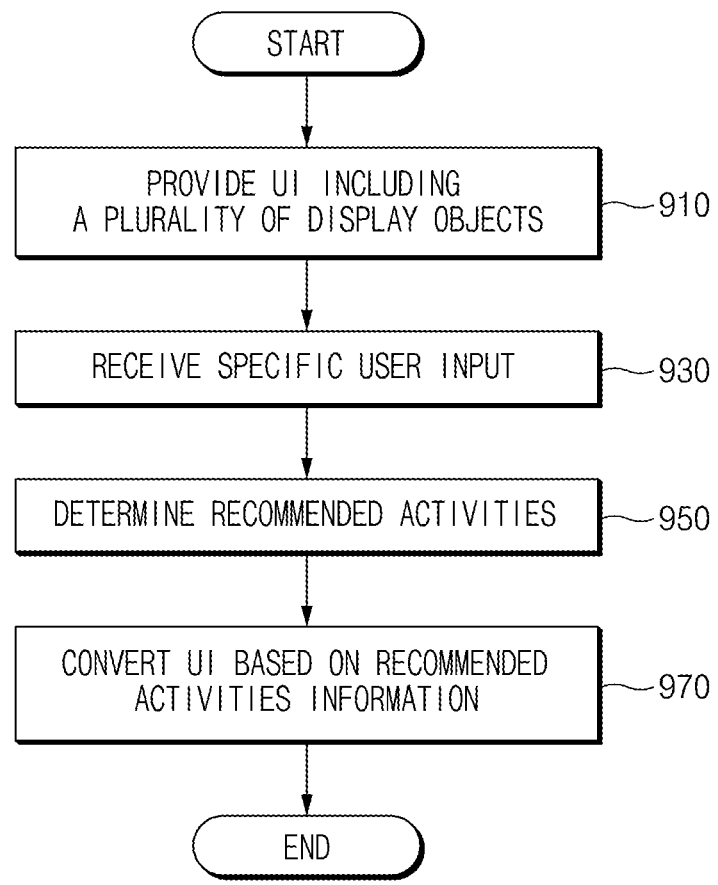
FIG. 9 is a flowchart illustrating an operation method of an electronic device associated with providing recommended activities information according to various embodiments of the present disclosure.

FIG. 9 is a flowchart illustrating an operation method of an electronic device associated with providing recommended activities information according to various embodiments of the present disclosure.

Referring to FIG. 9, in operation 910, an electronic device 100 of FIG. 1 may provide a UI including a plurality of display objects. According to an embodiment, the electronic device 100 may include the UI, including the plurality of display objects corresponding to physiological state information, in a specific screen and may output the specific screen on a display 130 of FIG. 1.

In operation 930, the electronic device 100 may receive a specific user input. According to an embodiment, the electronic device 100 may receive a gesture input on the UI or a motion input of the electronic device 100, and the like. The motion input may include an input of tilting, rotating, or shaking the electronic device 100 in a specific direction.

According to various embodiments of the present disclosure, in operation 950, the electronic device 100 may determine activities to be recommended to its user, based on the physiological state information in response to the user input. According to an embodiment, the electronic device 100 may specify the recommended activities in a different way based on a type of the user input. In this regard, the recommended activities may include walking activities, running activities, cycling activities, rest activities, sleeping activities, or fluid intake activities and the like. According to various embodiments, the electronic device 100 may specify the recommended activities using history information of physiological state information stored in a memory 170 of FIG. 1.

In operation 970, the electronic device 100 may convert a UI based on information about the recommended activities. According to an embodiment, the electronic device 100 may generate a UI including a display object corresponding to the recommended activities information and may convert a previously output UI into the newly generated UI.

Figure 10:
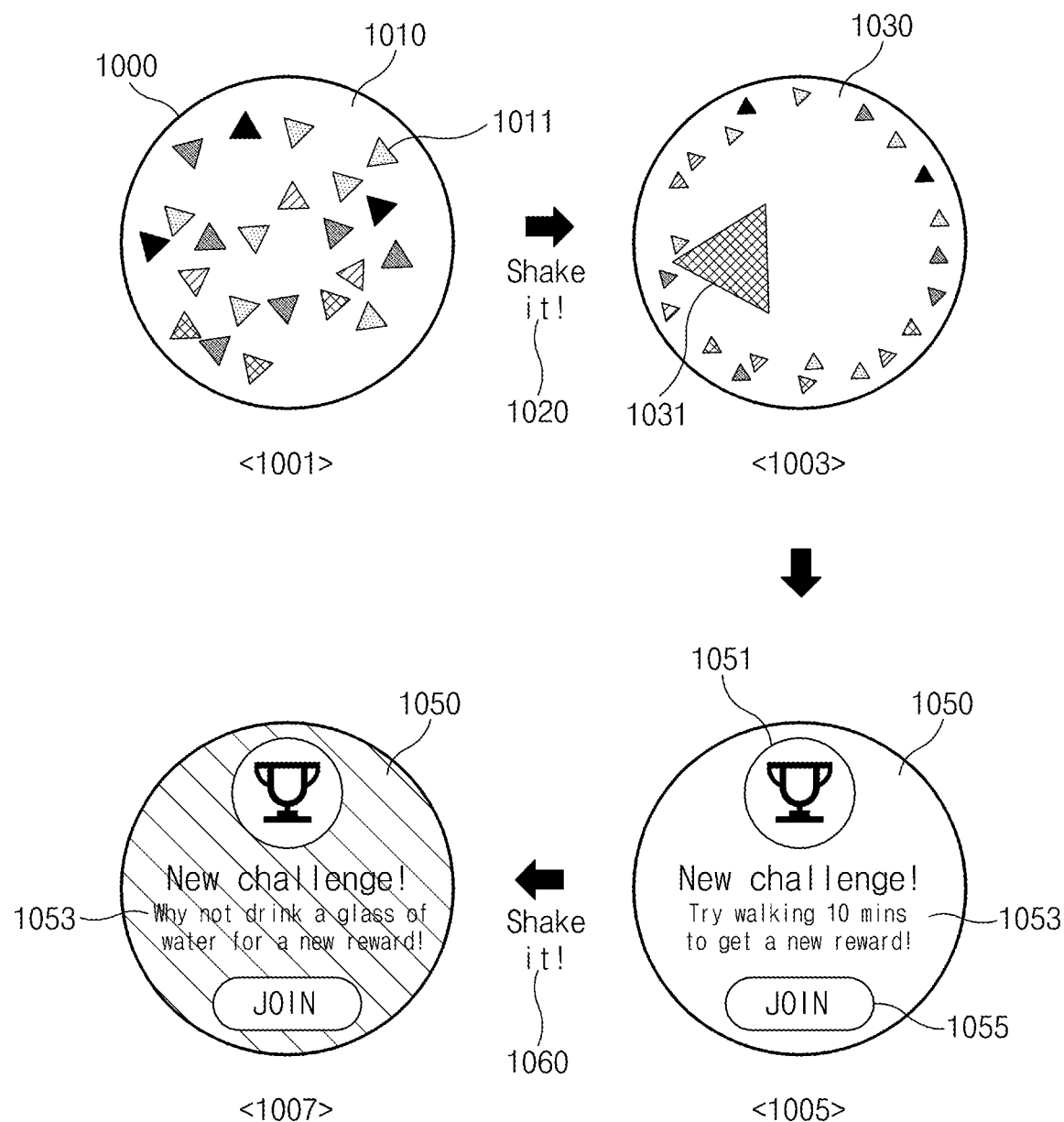
FIG. 10 is a drawing illustrating an operation of providing recommended activities information according to various embodiments of the present disclosure.

FIG. 10 is a drawing illustrating an operation of providing recommended activities information according to various embodiments of the present disclosure.

Referring to FIG. 10, in a first state 1001, an electronic device 100 of FIG. 1 may include a plurality of display objects 1011, corresponding to physiological state information, in a UI (e.g., a first UI 1010) and may display the UI on its display 1000. According to various embodiments, the electronic device 100 may receive a specific user input in the first state 1001.

Referring to FIG. 10, in an embodiment, an input 1020 may occur by shaking the electronic device 100.

Upon receiving the specific user input, such as input 1020, the electronic device 100 may determine activities to be recommended to its user. Also, in a second state 1003, the electronic device 100 may provide a UI (e.g., a second UI 1030) including a display object 1031 corresponding to information about the recommended activities. According to an embodiment, the electronic device 100 may include the display object 1031, corresponding to the recommended activities information, together with a display object, corresponding to another recommended activities information, in the second UI 1030. Alternatively, the electronic device 100 may include the display object 1031, corresponding to the recommend activities information, together with display objects, corresponding to physiological state information, in the second UI 1030. According to various embodiments, the electronic device 100 may generate the display object 1031 to be relatively larger in size than the other display objects and may output the generated display object 1031. Also, the electronic device 100 may move the other display objects to a rim of a screen and may move the display object 1031, corresponding to the recommended activities information, from the rim of the screen to the center of the screen to output the other display objects and the display object 1031.

According to various embodiments, if a certain time elapses after the user input occurs or if the display object 1031 corresponding to the recommended activities information is moved to the center of the screen to be displayed on the screen, in a third state 1005, the electronic device 100 may provide a UI (e.g., a third UI 1050) of describing the recommended activities. The third UI 1050 may include an image or icon 1051 indicating a type of the recommended activities, a text object 1053 indicating contents of the recommended activities, or a recommended activities approval button 1055 for approving the recommended activities, and the like.

According to various embodiments, the electronic device 100 may convert the third UI 1050 into the first UI 1010 in response to selection of the recommended activities approval button 1055. According to various embodiments, if a specific user input (e.g., an input 1060 for shaking the electronic device 100) is received in the third state 1005, as described in a fourth state 1007, the electronic device 100 may specify recommended activities different from the recommended activities and may change the third UI 1050 based on the other recommended activities. According to an embodiment, the electronic device 100 may change the contents, in the text object 1053 indicating the contents of the recommended activities, to contents of the other recommended activities. In various embodiments, the electronic device 100 may change a background color of the third UI 1050 based on the other recommended activities.

According to various embodiments, a method for providing physiological state information in a wearable electronic device may include providing a UI including a plurality of movable particles, measuring motion of the wearable electronic device, and reducing the number of the plurality of movable particles based on the measured result.

According to various embodiments, the method may further include outputting a notification object including information about the motion, if motion of a first level or less continues for a certain time or more.

According to various embodiments, the method may further include changing a background color of the UI, if motion which is greater than a second level continues for a certain time or more.

According to various embodiments, a method for providing physiological state information in a wearable electronic device may include providing a UI including a plurality of display objects corresponding to physiological state information, measuring motion of the wearable electronic device, changing a display state of at least one of the plurality of display objects based on the motion of the wearable electronic device, obtaining information about a physiological state, and converting the UI based on the information associated with the physiological state.

According to various embodiments, the method may further include specifying at least one of the number of the plurality of display objects or a location, a shape, a color, or a size of each of the plurality of display objects in a different way based on properties of the physiological state information.

According to various embodiments, the changing of the display state of the at least one of the plurality of display objects may include determining a walking state, a running state, a cycling state, a sitting state, or a sleeping state based on the motion information of the wearable electronic device and changing at least one of the number of the plurality of display objects or a location, a shape, a color, or a size of each of the plurality of display objects in a different way based on the determined state.

According to various embodiments, the obtaining of the information associated with the physiological state may include obtaining heartbeat information of a user of the wearable electronic device based on a heartbeat sensor of the wearable electronic device. The converting of the UI may include converting the UI into a UI of repeatedly changing at least one of a shape, a color, or a size of at least one of the plurality of display objects corresponding to a heartbeat pattern of the user based on the heartbeat information.

According to various embodiments, the obtaining of the information associated with the physiological state may include receiving a user input associated with setting a fluid intake time based on a touch sensor of the wearable electronic device. The converting of the UI may include converting the UI into a UI of changing at least one of the number of the plurality of display objects or a location, a shape, a color, or a size of each of the plurality of display objects to be different from the other display objects included in the UI, if the fluid intake time arrives or occurs.

According to various embodiments, the method may further include receiving a touch input on the UI and providing history information of the display object corresponding to a location of the touch input.

According to various embodiments, the method may further include receiving a motion input of the wearable electronic device and providing recommended activities information if motion of the wearable electronic device meets a specific condition.

Figure 11:
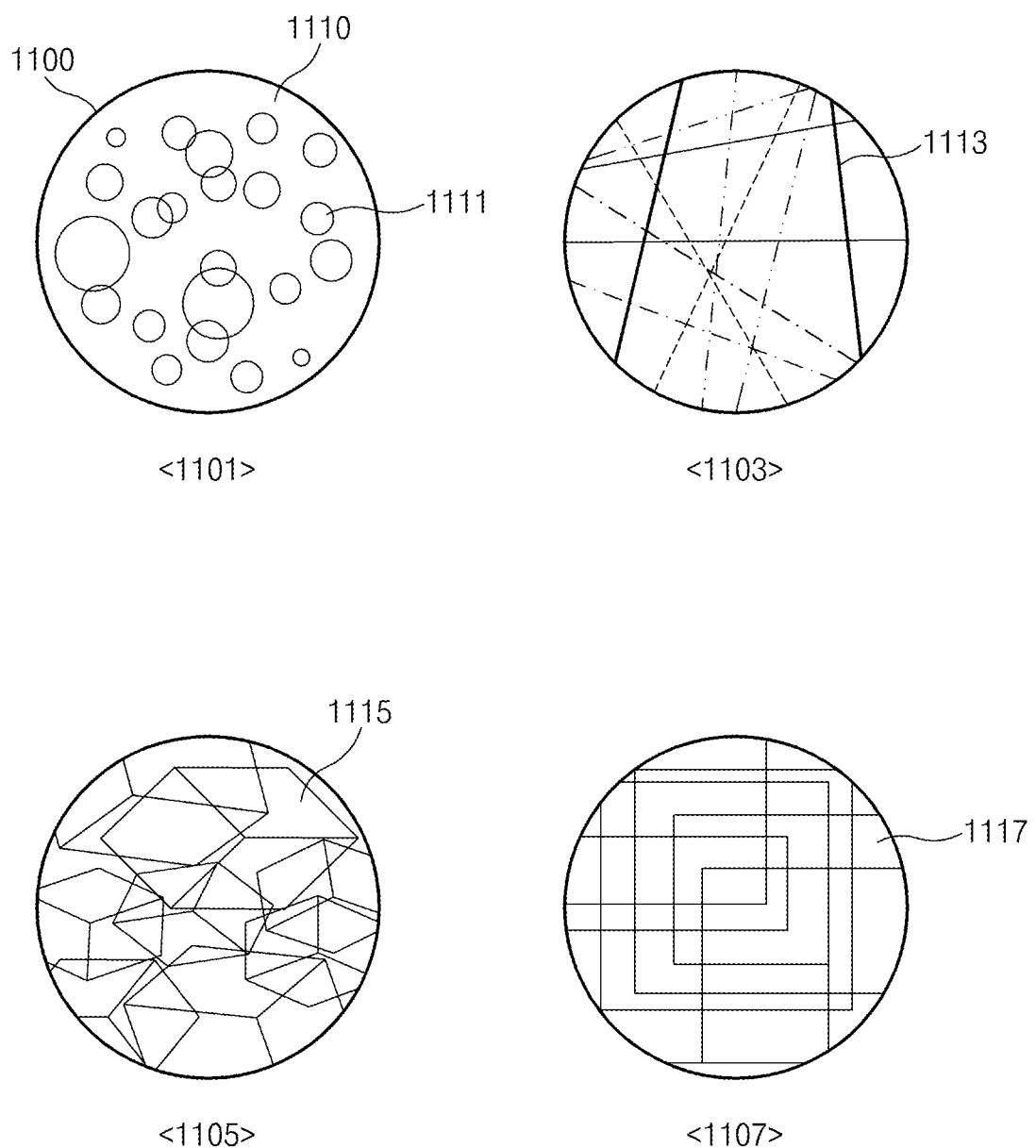
FIG. 11 is a drawing illustrating various forms of display objects included in a UI according to various embodiments of the present disclosure.

FIG. 11 is a drawing illustrating display various forms of objects included in a UI according to various embodiments of the present disclosure.

Referring to FIG. 11, an electronic device 100 of FIG. 1 may output a UI 1110, including a plurality of display objects, on its display 1100. In this case, the electronic device 100 may provide the plurality of display objects, included in the UI 1110, in various forms. For example, the electronic device 100 may provide a plurality of particle objects as the plurality of display objects. Alternatively, the electronic device 100 may provide a plurality of image objects, formed by points, lines, or faces, as the plurality of display objects.

According to various embodiments of the present disclosure, in a first state 1101, the electronic device 100 may include a plurality of particle objects 1111 in the UI 1110. Alternatively, in a second state 1103, the electronic device 100 may include a plurality of line image objects 1113 in the UI 1110. Alternatively, in a third state 1105, the electronic device 100 may include a plurality of polygonal image objects 1115, formed by lines and faces, in the UI 1110. In various embodiments, in a fourth state 1107, the electronic device 100 may designate each of a plurality of regions 1117, divided by a plurality of lines, as corresponding one display object. In this case, the electronic device 100 may specify each of the designated display objects to have different colors or size and the like per each region.

Figure 12:
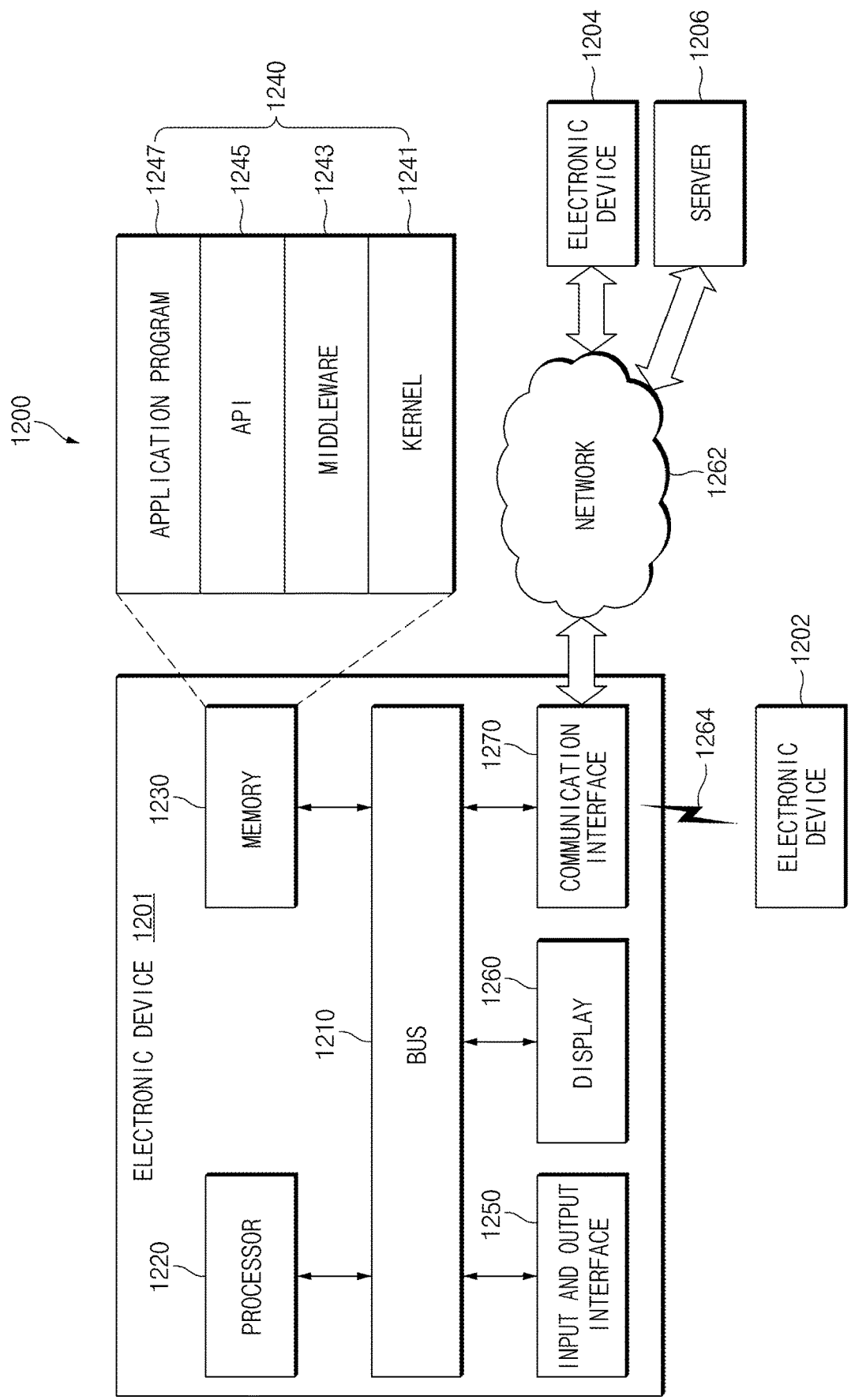
FIG. 12 is a block diagram illustrating a configuration of an electronic device in a network environment according to various embodiments of the present disclosure.

FIG. 12 is a block diagram illustrating a configuration of an electronic device in a network environment according to various embodiments of the present disclosure.

A description will be given of an electronic device 1201 in a network environment 1200 with reference to FIG. 12 according to various embodiments. According to various embodiments, the electronic device 1201 may have the same or similar configuration to an electronic device 100 shown in FIG. 1. For example, the electronic device 1201 may perform the same or similar function to the electronic device 100 shown in FIG. 1. The electronic device 1201 may include a bus 1210, a processor 1220, a memory 1230, an input and output interface 1250, a display 1260, and a communication interface 1270. In various embodiments, at least one of the components of the electronic device 1201 may be omitted from the electronic device 1201, and other components may be additionally included in the electronic device 1201.

The bus 1210 may include, for example, a circuit which connects the components 1220 to 1270 with each other and sends a communication signal (e.g., a control message and/or data) between the components 1220 to 1270.

The processor 1220 may include one or more of a CPU, an application processor (AP), or a communication processor (CP). The processor 1220 may perform, for example, calculation or data processing about control and/or communication of at least another of the components of the electronic device 1201.

The memory 1230 may include a volatile and/or non-volatile memory. The memory 1230 may store, for example, a command or data associated with at least another of the components of the electronic device 1201. According to an embodiment, the memory 1230 may software and/or a program 1240. The program 1240 may include, for example, a kernel 1241, a middleware 1243, an application programming interface (API) 1245, and/or at least one application program 1247 (or "at least one application"), and the like. At least part of the kernel 1241, the middleware 1243, or the API 1245 may be referred to as an operating system (OS).

The kernel 1241 may control or manage, for example, system resources (e.g., the bus 1210, the processor 1220, or the memory 1230, and the like) used to execute an operation or function implemented in the other programs (e.g., the middleware 1243, the API 1245, or the application program 1247). Also, as the middleware 1243, the API 1245, or the application program 1247 accesses a separate component of the electronic device 1201, the kernel 1241 may provide an interface which may control or manage system resources.

The middleware 1243 may play a role as, for example, a go-between such that the API 1245 or the application program 1247 communicates with the kernel 1241 to communicate data with the kernel 1241.

Also, the middleware 1243 may process one or more work requests, received from the application program 1247, in order of priority. For example, the middleware 1243 may assign priority which may use system resources (the bus 1210, the processor 1220, or the memory 1230, and the like) of the electronic device 1201 to at least one of the at least one application program 1247. For example, the middleware 1243 may perform scheduling or load balancing for the one or more work requests by processing the one or more work requests in order of priority assigned to the at least one of the at least one application program 1247.

The API 1245 may be, for example, an interface in which the application program 1247 controls a function provided from the kernel 1241 or the middleware 1243. For example, the API 1245 may include at least one interface or function (e.g., instruction) for file control, window control, image processing, or text control, and the like.

The input and output interface 1250 may play a role as, for example, an interface which may send a command or data, input from a user or another external device, to another component (or other components) of the electronic device 1201. Also, the input and output interface 1250 may output a command or data, received from another component (or other components) of the electronic device 1201, to the user or the other external device.

The display 1260 may include, for example, a liquid crystal display (LCD), a light emitting diode (LED) display, an organic LED (OLED) display, a microelectromechanical systems (MEMS) display, or an electronic paper display. The display 1260 may display, for example, a variety of content (e.g., text, images, videos, icons, or symbols, and the like) to the user. The display 1260 may include a touch screen, and may receive, for example, a touch, a gesture, proximity, or a hovering input using an electronic pen or part of a body of the user.

The communication interface 1270 may establish communication between, for example, the electronic device 1201 and an external device (e.g., a first external electronic device 1202, a second external electronic device 1204, or a server 1206). For example, the communication interface 1270 may connect to a network 1262 through wireless communication or wired communication and may communicate with the external device (e.g., the second external electronic device 1204 or the server 1206).

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. Also, the wireless communication may include, for example, local-area communication 1264. The local-area communication 1264 may include, for example, at least one of Wi-Fi communication, Bluetooth (BT) communication, near field communication (NFC) communication, or GNSS communication, and the like. The GNSS may include, for example, at least one of a global positioning system (GPS), a Glonass, a Beidou navigation satellite system (hereinafter referred to as "Beidou"), or a Galileo (i.e., the European global satellite-based navigation system). Hereinafter, the "GPS" used herein may be interchangeably with the "GNSS". The wired communication may include, for example, at least one of universal serial bus (USB) communication, high definition multimedia interface (HDMI) communication, recommended standard 232 (RS-232) communication, power line communication, or plain old telephone service (POTS) communication, and the like. The network 1262 may include a telecommunications network, for example, at least one of a computer network (e.g., a local area network (LAN) or a wide area network (WAN)), the Internet, or a telephone network.

Each of the first and second external electronic devices 1202 and 1204 may be the same as or different device from the electronic device 1201. According to an embodiment, the server 1206 may include a group of one or more servers. According to various embodiments, all or some of operations executed in the electronic device 1201 may be executed in another electronic device or a plurality of electronic devices (e.g., the first external electronic device 1202, the second external electronic device 1204, or the server 1206). According to an embodiment, if the electronic device 1201 should perform any function or service automatically or according to a request, it may request another device (e.g., the first external electronic device 1202, the second external electronic device 1204, or the server 1206) to perform at least part of the function or service, rather than executing the function or service for itself or in addition to the function or service. The other electronic device (e.g., the first external electronic device 1202, the second external electronic device 1204, or the server 1206) may execute the requested function or the added function and may transmit the executed result to the electronic device 1201. The electronic device 1201 may process the received result without change or additionally and may provide the requested function or service. For this purpose, for example, cloud computing technologies, distributed computing technologies, or client-server computing technologies may be used.

Figure 13:
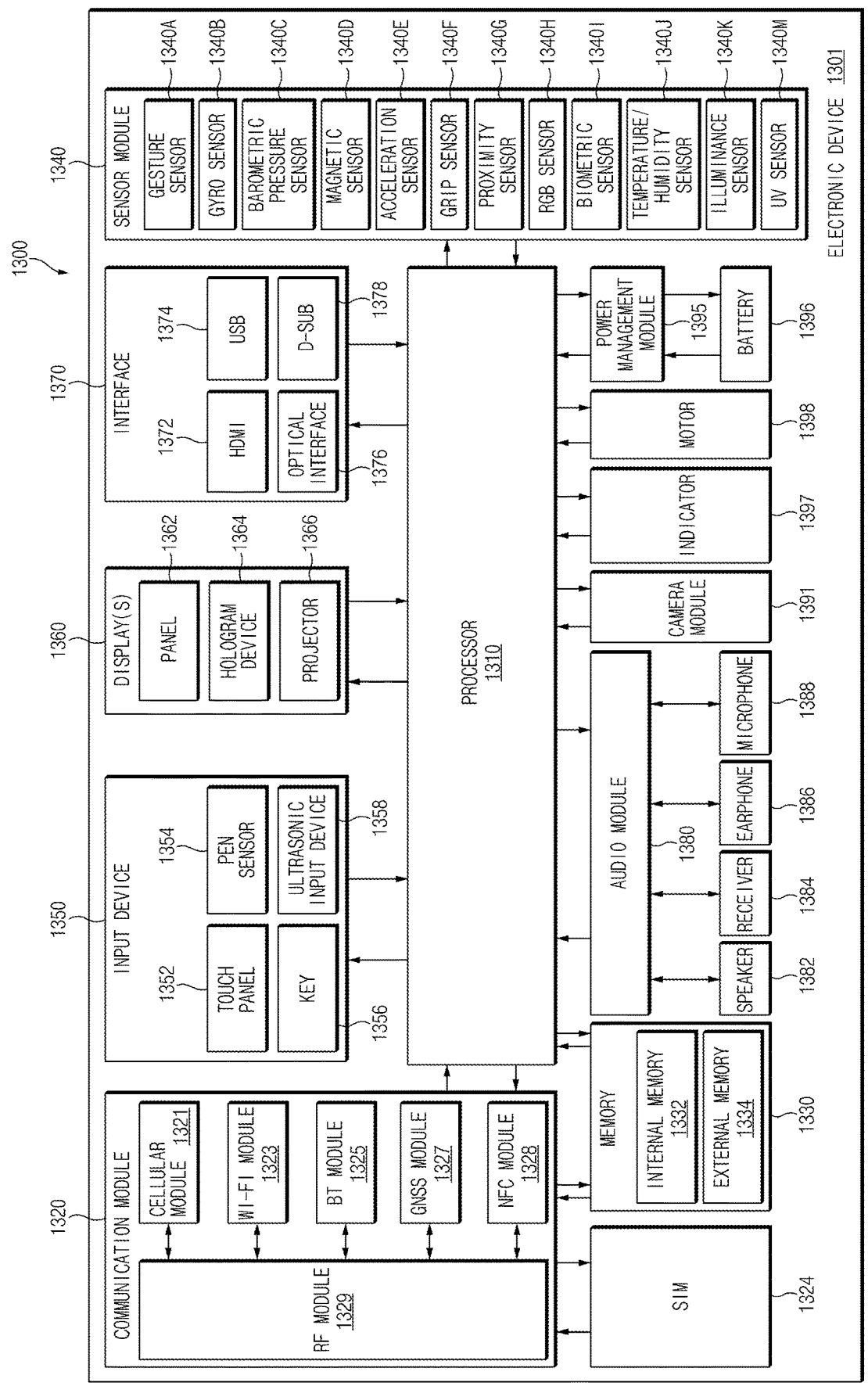
FIG. 13 is a block diagram illustrating a configuration of an electronic device according to various embodiments of the present disclosure.

FIG. 13 is a block diagram illustrating a configuration of an electronic device according to various embodiments of the present disclosure.

Referring to FIG. 13, an electronic device 1301 may include, for example, all or part of an electronic device 1201 shown in FIG. 12. The electronic device 1301 may include one or more processors 1310 (e.g., APs), a communication module 1320, a subscriber identification module (SIM) 1324, a memory 1330, a sensor module 1340, an input device 1350, a display 1360, an interface 1370, an audio module 1380, a camera module 1391, a power management module 1395, a battery 1396, an indicator 1397, and a motor 1398.

The processor 1310 may execute, for example, an OS or an application program to control a plurality of hardware or software components connected thereto and may process and compute a variety of data. The processor 1310 may be implemented with, for example, a system on chip (SoC). According to an embodiment, the processor 1310 may include a graphic processing unit (GPU) (not shown) and/or an image signal processor (ISP) (not shown). The processor 1310 may include at least some (e.g., a cellular module 1321) of the components shown in FIG. 13. The processor 1310 may load a command or data, received from at least one of other components (e.g., a non-volatile memory), to a volatile memory to process the data and may store various data in a non-volatile memory.

The communication module 1320 may have the same or similar configuration to a communication interface 1270 of FIG. 12. The communication module 1320 may include, for example, the cellular module 1321, a Wi-Fi module 1323, a BT module 1325, a GNSS module 1327 (e.g., a GPS module, a Glonass module, a Beidou module, or a Galileo module), a NFC module 1328, and a radio frequency (RF) module 1329.

The cellular module 1321 may provide, for example, a voice call service, a video call service, a text message service, or an Internet service, and the like through a communication network. According to an embodiment, the cellular module 1321 may identify and authenticate the electronic device 1301 in a communication network using a SIM 1324 (e.g., a SIM card). According to an embodiment, the cellular module 1321 may perform at least some of functions which may be provided by the processor 1310. According to an embodiment, the cellular module 1321 may include a CP.

The Wi-Fi module 1323, the BT module 1325, the GNSS module 1327, or the NFC module 1328 may include, for example, a processor for processing data communicated through the corresponding module. According to various embodiments, at least some (e.g., two or more) of the cellular module 1321, the Wi-Fi module 1323, the BT module 1325, the GNSS module 1327, or the NFC module 1328 may be included in one integrated chip (IC) or one IC package.

The RF module 1329 may communicate, for example, a communication signal (e.g., an RF signal). Though not shown, the RF module 1329 may include, for example, a transceiver, a power amplifier module (PAM), a frequency filter, or a low noise amplifier (LNA), or an antenna, and the like. According to another embodiment, at least one of the cellular module 1321, the Wi-Fi module 1323, the BT module 1325, the GNSS module 1327, or the NFC module 1328 may communicate an RF signal through a separate RF module.

The SIM 1324 may include, for example, a card which includes a SIM and/or an embedded SIM. The SIM 1324 may include unique identification information (e.g., an integrated circuit card identifier (ICCID)) or subscriber information (e.g., an international mobile subscriber identity (IMSI)).

The memory 1330 (e.g., a memory 1230 of FIG. 12) may include, for example, an internal memory 1332 or an external memory 1334. The internal memory 1332 may include at least one of, for example, a volatile memory (e.g., a dynamic random access memory (DRAM), a static RAM (SRAM), a synchronous dynamic RAM (SDRAM), and the like), or a non-volatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory, and the like), a hard drive, or a solid state drive (SSD)).

The external memory 1334 may include a flash drive, for example, a compact flash (CF), a secure digital (SD), a micro-SD, a mini-SD, an extreme digital (xD), a multimedia card (MMC), or a memory stick, and the like. The external memory 1334 may operatively and/or physically connect with the electronic device 1301 through various interfaces.

The sensor module 1340 may measure, for example, a physical quantity or may detect an operation state of the electronic device 1301, and may convert the measured or detected information to an electric signal. The sensor module 1340 may include at least one of, for example, a gesture sensor 1340A, a gyro sensor 1340B, a barometric pressure sensor 1340C, a magnetic sensor 1340D, an acceleration sensor 1340E, a grip sensor 1340F, a proximity sensor 1340G, a color (RGB) sensor 1340H (e.g., red, green, blue (RGB) sensor), a biometric sensor 1340I, a temperature/humidity sensor 1340J, an illuminance sensor 1340K, or an ultraviolet (UV) sensor 1340M. Additionally or alternatively, the sensor module 1340 may further include, for example, an e-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), and/or a fingerprint sensor (not shown), and the like. The sensor module 1340 may further include a control circuit for controlling at least one or more sensors included therein. In various embodiments, the electronic device 1301 may further include a processor configured to control the sensor module 1340, as part of the processor 1310 or to be independent of the processor 1310. While the processor 1310 is in a sleep state, the electronic device 1301 may control the sensor module 1340.

The input device 1350 may include, for example, a touch panel 1352, a pen sensor 1354, a key 1356, or an ultrasonic input unit 1358. The touch panel 1352 may use, for example, at least one of a capacitive type, a resistive type, an infrared type, or an ultrasonic type. Also, the touch panel 1352 may further include a control circuit. The touch panel 1352 may further include a tactile layer and may provide a tactile reaction to a user.

The pen sensor 1354 may be, for example, part of the touch panel 1352 or may include a separate sheet for recognition. The key 1356 may include, for example, a physical button, an optical key, or a keypad. The ultrasonic input unit 1358 may allow the electronic device 1301 to detect an ultrasonic wave generated by an input tool, through a microphone (e.g., a microphone 1388) and to verify data corresponding to the detected ultrasonic wave.

The display 1360 (e.g., a display 1260 of FIG. 12) may include a panel 1362, a hologram device 1364, or a projector 1366. The panel 1362 may include the same or similar configuration to the display 1360. The panel 1362 may be implemented to be, for example, flexible, transparent, or wearable. The panel 1362 and the touch panel 1352 may be integrated into one module. The hologram device 1364 may show a stereoscopic image in a space using interference of light. The projector 1366 may project light onto a screen to display an image. The screen may be positioned, for example, inside or outside the electronic device 1301. According to an embodiment, the display 1360 may further include a control circuit for controlling the panel 1362, the hologram device 1364, or the projector 1366.

The interface 1370 may include, for example, a HDMI 1372, a USB 1374, an optical interface 1376, or a D-subminiature 1378. The interface 1370 may be included in, for example, a communication interface 1270 shown in FIG. 12. Additionally or alternatively, the interface 1370 may include, for example, a mobile high definition link (MHL) interface, an SD card/multimedia card (MMC) interface, or an infrared data association (IrDA) standard interface.

The audio module 1380 may convert a sound and an electric signal in dual directions. At least some of components of the audio module 1380 may be included in, for example, an input and output interface 1250 shown in FIG. 12. The audio module 1380 may process sound information input or output through, for example, a speaker 1382, a receiver 1384, an earphone 1386, or the microphone 1388, and the like.

The camera module 1391 may be a device which captures a still image and a moving image. According to an embodiment, the camera module 1391 may include one or more image sensors (not shown) (e.g., a front sensor or a rear sensor), a lens (not shown), an ISP (not shown), or a flash (not shown) (e.g., an LED or a xenon lamp).

The power management module 1395 may manage, for example, power of the electronic device 1301. According to an embodiment, though not shown, the power management module 1395 may include a power management integrated circuit (PMIC), a charger IC or a battery or fuel gauge. The PMIC may have a wired charging method and/or a wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided. The battery gauge may measure, for example, the remaining capacity of the battery 1396 and voltage, current, or temperature thereof while the battery 1396 is charged. The battery 1396 may include, for example, a rechargeable battery or a solar battery.

The indicator 1397 may display a specific state of the electronic device 1301 or part (e.g., the processor 1310) thereof, for example, a booting state, a message state, or a charging state, and the like. The motor 1398 may convert an electric signal into mechanical vibration and may generate vibration or a haptic effect, and the like. Though not shown, the electronic device 1301 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a mediaFlo™ standard, and the like.

Each of the above-mentioned elements of the electronic device according to various embodiments of the present disclosure may be configured with one or more components, and names of the corresponding elements may be changed according to the type of the electronic device. The electronic device according to various embodiments of the present disclosure may include at least one of the above-mentioned elements, some elements may be omitted from the electronic device, or other additional elements may be further included in the electronic device. Also, some of the elements of the electronic device according to various embodiments of the present disclosure may be combined with each other to form one entity, thereby making it possible to perform the functions of the corresponding elements in the same manner as before the combination.

Figure 14:
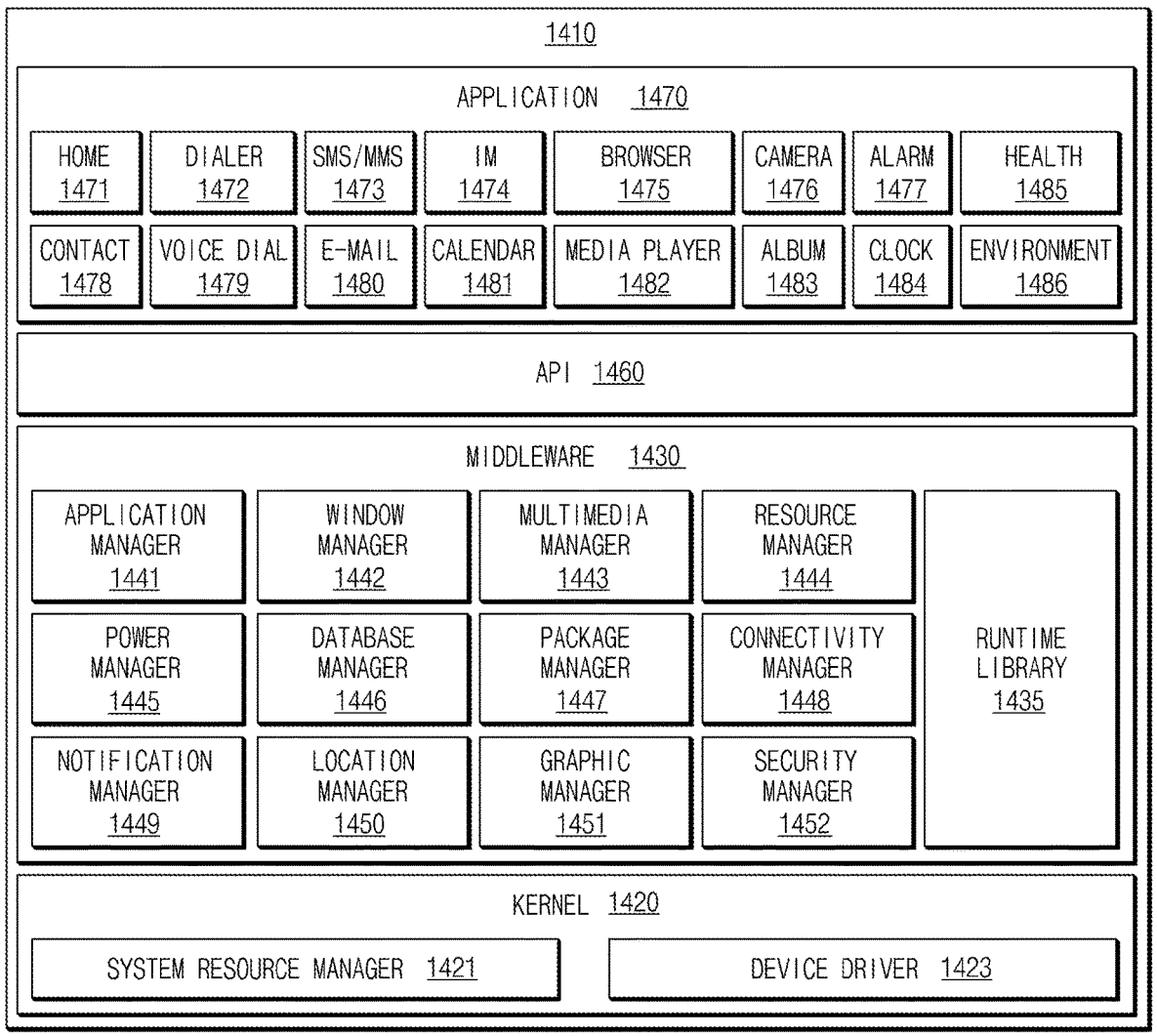
FIG. 14 is a block diagram illustrating a configuration of a program module according to various embodiments of the present disclosure.

FIG. 14 is a block diagram illustrating a configuration of a program module according to various embodiments of the present disclosure.

According to an embodiment, a program module 1410 (e.g., a program 1240 of FIG. 12) may include an OS for controlling resources associated with an electronic device (e.g., an electronic device 1201 of FIG. 12) and/or various applications (e.g., at least one application program 1247 of FIG. 12) which are executed on the OS. The OS may be, for example, Android™, iOS™, Windows™, Symbian™, Tizen™, or Bada™, and the like.

Referring to FIG. 14, the program module 1410 may include a kernel 1420, a middleware 1430, an application programming interface (API) 1460, and/or at least one application 1470. At least part of the program module 1410 may be preloaded on the electronic device, or may be downloaded from an external electronic device (e.g., a first external electronic device 1202, a second external electronic device 1204, or a server 1206, and the like of FIG. 12).

The kernel 1420 (e.g., a kernel 1241 of FIG. 12) may include, for example, a system resource manager 1421 and/or a device driver 1423. The system resource manager 1421 may control, assign, or collect, and the like system resources. According to an embodiment, the system resource manager 1421 may include a process management unit, a memory management unit, or a file system management unit, and the like. The device driver 1423 may include, for example, a display driver, a camera driver, a BT driver, a shared memory driver, a USB driver, a keypad driver, a Wi-Fi driver, an audio driver, or an inter-process communication (IPC) driver.

The middleware 1430 (e.g., a middleware 1243 of FIG. 12) may provide, for example, functions the application 1470 needs in common, and may provide various functions to the application 1470 through the API 1460 such that the application 1470 efficiently uses limited system resources in the electronic device. According to an embodiment, the middleware 1430 (e.g., the middleware 1243) may include at least one of a runtime library 1435, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, or a security manager 1452.

The runtime library 1435 may include, for example, a library module used by a compiler to add a new function through a programming language while the application 1470 is executed. The runtime library 1435 may perform a function about input and output management, memory management, or an arithmetic function.

The application manager 1441 may manage, for example, a life cycle of at least one of the at least one application 1470. The window manager 1442 may manage graphic user interface (GUI) resources used on a screen of the electronic device. The multimedia manager 1443 may ascertain a format necessary for reproducing various media files and may encode or decode a media file using a codec corresponding to the corresponding format. The resource manager 1444 may manage source codes of at least one of the at least one application 1470, and may manage resources of a memory or a storage space, and the like.

The power manager 1445 may act together with, for example, a basic input/output system (BIOS) and the like, may manage a battery or a power source, and may provide power information necessary for an operation of the electronic device. The database manager 1446 may generate, search, or change a database to be used in at least one of the at least one application 1470. The package manager 1447 may manage installation or update of an application distributed by a type of a package file.

The connectivity manager 1448 may manage, for example, wireless connection such as Wi-Fi connection or BT connection, and the like. The notification manager 1449 may display or notify events, such as an arrival message, an appointment, and proximity notification, by a method which is not disturbed to the user. The location manager 1450 may manage location information of the electronic device. The graphic manager 1451 may manage a graphic effect to be provided to the user or a user interface (UI) related to the graphic effect. The security manager 1452 may provide all security functions necessary for system security or user authentication, and the like. According to an embodiment, when the electronic device (e.g., an electronic device 1201 of FIG. 12) has a phone function, the middleware 1430 may further include a telephony manager (not shown) for managing a voice or video communication function of the electronic device.

The middleware 1430 may include a middleware module which configures combinations of various functions of the above-described components. The middleware 1430 may provide a module which specializes according to kinds of OSs to provide a differentiated function. Also, the middleware 1430 may dynamically delete some of old components or may add new components.

The API 1460 (e.g., an API 1245 of FIG. 12) may be, for example, a set of API programming functions, and may be provided with different components according to OSs. For example, in case of Android or iOS, one API set may be provided according to platforms. In case of Tizen™, two or more API sets may be provided according to platforms.

The application 1470 (e.g., an application program 1247 of FIG. 12) may include one or more of, for example, a home application 1471, a dialer application 1472, a short message service/multimedia message service (SMS/MMS) application 1473, an instant message (IM) application 1474, a browser application 1475, a camera application 1476, an alarm application 1477, a contact application 1478, a voice call application 1479, an e-mail application 1480, a calendar application 1481, a media player application 1482, an album application 1483, a clock application 1484, a health care application (health 1485) (e.g., an application for measuring quantity of exercise or blood sugar, and the like), or an environment information application (environment 1486) (e.g., an application for providing atmospheric pressure information, humidity information, or temperature information, and the like), and the like.

According to an embodiment, the application 1470 may include an application (hereinafter, for better understanding and ease of description, referred to as "information exchange application") for exchanging information between the electronic device (e.g., the electronic device 1201) and an external electronic device (e.g., the first external electronic devices 1202 or the second external electronic device 1204). The information exchange application may include, for example, a notification relay application for transmitting specific information to the external electronic device or a device management application for managing the external electronic device.

For example, the notification relay application may include a function of transmitting notification information, which is generated by other applications (e.g., the SMS/MMS application, the e-mail application, the health care application, or the environment information application, and the like) of the electronic device, to the external electronic device (e.g., the first external electronic devices 1202 or the second external electronic device 1204). Also, the notification relay application may receive, for example, notification information from the external electronic device, and may provide the received notification information to the user of the electronic device.

The device management application may manage (e.g., install, delete, or update), for example, at least one (e.g., a function of turning on/off the external electronic device itself (or partial components) or a function of adjusting brightness (or resolution) of a display) of functions of the external electronic device (e.g., the first external electronic devices 1202 or the second external electronic device 1204) which communicates with the electronic device, an application which operates in the external electronic device, or a service (e.g., a call service or a message service) provided from the external electronic device.

According to an embodiment, the application 1470 may include an application (e.g., the health card application of a mobile medical device) which is preset according to attributes of the external electronic device (e.g., the first external electronic devices 1202 or the second external electronic device 1204). According to an embodiment of the present disclosure, the application 1470 may include an application received from the external electronic device (e.g., the server 1206, the first external electronic devices 1202, or the second external electronic device 1204). According to an embodiment of the present disclosure, the application 1470 may include a preloaded application or a third party application which may be downloaded from a server. Names of the components of the program module 1410 according to various embodiments of the present disclosure may differ according to kinds of OSs.

According to various embodiments, at least part of the program module 1410 may be implemented with software, firmware, hardware, or at least two or more combinations thereof. At least part of the program module 1410 may be implemented (e.g., executed) by, for example, a processor (e.g., a processor 1310 of FIG. 13). At least part of the program module 1410 may include, for example, a module, a program, a routine, sets of instructions, or a process, and the like for performing one or more functions.

The terminology "module" used herein may mean, for example, a unit including one of hardware, software, and firmware or two or more combinations thereof. The terminology "module" may be interchangeably used with, for example, terminologies "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of an application-specific integrated circuit (ASIC) chip, field-programmable gate arrays (FPGAs), or a programmable-logic device, which is well known or will be developed in the future, for performing certain operations.

According to various embodiments, at least part of a device (e.g., modules or the functions) or a method (e.g., operations) may be implemented with, for example, instructions stored in computer-readable storage media which have a program module. When the instructions are executed by a processor (e.g., a processor 1220 of FIG. 12), one or more processors may perform functions corresponding to the instructions. The computer-readable storage media may be, for example, a memory 1230 of FIG. 12.

The computer-readable storage media may include a hard disc, a floppy disk, magnetic media (e.g., a magnetic tape), optical media (e.g., a compact disc ROM (CD-ROM) and a DVD), magneto-optical media (e.g., a floptical disk), a hardware device (e.g., a ROM, a random access memory (RAM), or a flash memory, and the like), and the like. Also, the program instructions may include not only mechanical codes compiled by a compiler but also high-level language codes which may be executed by a computer using an interpreter and the like. The above-mentioned hardware device may be configured to operate as one or more software modules to perform operations according to various embodiments of the present disclosure, and vice versa.

According to various embodiments, the electronic device may provide a physiological state in an allusive way by providing a UI including a display object corresponding to physiological state information and changing the UI or a display object included in the UI based on a change of the physiological state.

Modules or program modules according to various embodiments may include at least one or more of the above-mentioned components, some of the above-mentioned components may be omitted, or other additional components may be further included. Operations executed by modules, program modules, or other components may be executed by a successive method, a parallel method, a repeated method, or a heuristic method. Also, some operations may be executed in a different order or may be omitted, and other operations may be added.

While the present disclosure has been shown and described with reference to various embodiments thereof, it will be understood by those skilled in the art that various changes in form and details may be made therein without departing from the spirit and scope of the present disclosure as defined in the appended claims and their equivalents.

What is claimed is:

1. A wearable electronic device comprising:
a plurality of sensors;
a display; and
a processor configured to:
obtain physiological state information related to a plurality of physiological states of a user of the wearable electronic device through the plurality of sensors,
control the display to provide a user interface (UI) including a plurality of movable display objects corresponding to each of the plurality of physiological states, wherein, based upon properties of the physiological state information, the plurality of moveable display objects varies in at least one of a number, a location, a shape, a color, or a size,
change at least one of the number, the location, the shape, the color, or the size of the plurality of movable display objects upon analyzing the obtained physiological information, and
change a state of the UI such that a position of the plurality of movable display objects corresponds to a direction of a sensed motion of the wearable electronic device.

2. The wearable electronic device of claim 1, wherein the at least one of a number, a location, a shape, a color, and a size of a display object corresponding to a first physiological state among the plurality of physiological states, is different from a number, a location, a shape, a color, and a size of a display object corresponding to a second physiological state among the plurality of physiological states.

3. The wearable electronic device of claim 1,
wherein the plurality of sensors comprises an acceleration sensor to obtain the direction of the sensed motion of the wearable electronic device, and
wherein the processor is further configured to:
determine at least one of a walking state, a running state, a cycling state, a sitting state, or a sleeping state based on the sensed motion of the wearable electronic device, and
change at least one of the number of the plurality of movable display objects, a location, a shape, a color, or a size of each of the plurality of movable display objects in a different way based on the obtained physiological state information.

4. The wearable electronic device of claim 1,
wherein the plurality of sensors comprises a heartbeat sensor to obtain heartbeat information of a user of the wearable electronic device, and
wherein the processor is further configured to repeatedly change at least one of a shape, a color, or a size of at least one of the plurality of movable display objects in response to a heartbeat pattern of the user based on the heartbeat information.

5. The wearable electronic device of claim 1,
wherein the plurality of sensors comprises a touch sensor to receive a user input associated with setting a fluid intake time, and
wherein the processor is further configured to change at least one of the number of the plurality of movable display objects or a location, a shape, a color, or a size of each of the plurality of movable display objects based on the fluid intake time.

6. The wearable electronic device of claim 4,
wherein the plurality of sensors includes a touch sensor to receive a touch input on the UI, and
wherein the processor is further configured to provide history information of a display object corresponding to a location of the touch input among the plurality of movable display objects based on receipt of the touch input.

7. The wearable electronic device of claim 1, wherein the processor is further configured to provide recommended activities information based on the motion of the wearable electronic device meeting a specified condition.

8. A method for providing physiological state information in a wearable electronic device, the method comprising:
obtaining physiological state information related to a plurality of physiological states of a user of the wearable electronic device through a plurality of sensors of the wearable electronic device;
providing a user interface (UI) including a plurality of movable display objects corresponding to each of the plurality of physiological states, wherein, based upon properties of the physiological state information, the plurality of moveable display objects varies in at least one of a number, a location, a shape, a color, or a size;
changing at least one of the number, the location, the shape, the color, or the size of the plurality of movable display objects upon analyzing the obtained physiological state information;
measuring motion and a direction of the motion of the wearable electronic device;
changing a display state of the UI such that a position of the plurality of movable display objects, corresponds to the measured direction of the motion of the wearable electronic device; and
converting the UI based on the obtained physiological state information,
wherein the plurality of movable display objects includes a plurality of movable particles.

9. The method of claim 8, wherein the changing of the display state of the at least one of the plurality of movable display objects comprises reducing the number of the plurality of movable particles based on the measured motion of the wearable electronic device.

10. The method of claim 8, further comprising:
outputting a notification object including information about the motion, based on the motion classified as a first level or lower continuing for a specified time or more.

11. The method of claim 8, further comprising:
changing a background color of the UI, based on the motion classified as being greater than a second level continuing for a specified time or more.

12. The method of claim 8, wherein the changing of the display state of the at least one of the plurality of movable display objects comprises:
determining a walking state, a running state, a cycling state, a sitting state, or a sleeping state, based on the measured motion of the wearable electronic device; and
changing at least one of the number of the plurality of movable display objects or a location, a shape, a color, or a size of each of the plurality of movable display objects in a different way based on the determined state.

13. The method of claim 8,
wherein the obtaining of the physiological state information related to the plurality of physiological states comprises obtaining heartbeat information of a user of the wearable electronic device based on a heartbeat sensor of the wearable electronic device, and
wherein the converting of the UI comprises converting the UI into a UI for repeatedly changing at least one of a shape, a color, or a size of at least one of the plurality of movable display objects in response to a heartbeat pattern of the user based on the heartbeat information.

14. The method of claim 8,
wherein the obtaining of physiological state information related to the plurality of physiological states comprises receiving a user input associated with setting a fluid intake time based on a touch sensor of the wearable electronic device, and
wherein the converting of the UI comprises converting the UI into a UI for changing at least one of the number of the plurality of moveable display objects or a location, a shape, a color, or a size of each of the plurality of moveable display objects based on the fluid intake time.

15. The method of claim 8, further comprising:
receiving a touch input on the UI; and
providing history information of a display object corresponding to a location of the touch input among the plurality of moveable display objects.

16. The method of claim 8, further comprising:
receiving a motion input of the wearable electronic device; and
providing recommended activities information, based on the motion input of the wearable electronic device meeting a specified condition.

* * * * *